United States Patent
Seki et al.

(10) Patent No.: US 9,551,672 B2
(45) Date of Patent: Jan. 24, 2017

(54) DEFECT CLASSIFYING METHOD AND OPTICAL INSPECTION APPARATUS FOR SILICON CARBIDE SUBSTRATE

(71) Applicant: Lasertec Corporation, Yokohama (JP)

(72) Inventors: Hirokazu Seki, Kanagawa (JP); Masamichi Shinoda, Yokohama (JP); Toshiyuki Todoroki, Yokohama (JP); Yoshihiro Nakano, Kanagawa (JP); Makoto Torizawa, Yokohama (JP)

(73) Assignee: Lasertec Corporation (JP)

( * ) Notice: Subject to any disclaimer, the term of this patent is extended or adjusted under 35 U.S.C. 154(b) by 225 days.

(21) Appl. No.: 14/574,641

(22) Filed: Dec. 18, 2014

(65) Prior Publication Data

US 2015/0168311 A1    Jun. 18, 2015

(30) Foreign Application Priority Data

Dec. 18, 2013   (JP) .................................. 2013-261652
Sep. 30, 2014   (JP) .................................. 2014-199771

(51) Int. Cl.
   *G01N 21/95*   (2006.01)
   *G01N 21/64*   (2006.01)

(52) U.S. Cl.
   CPC ...... *G01N 21/9501* (2013.01); *G01N 21/6489* (2013.01)

(58) Field of Classification Search
   CPC . G01N 21/00; G01N 21/8851; G01N 21/9501
   USPC ...................................................... 356/237.2
   See application file for complete search history.

(56) References Cited

U.S. PATENT DOCUMENTS

| 5,859,364 A * | 1/1999 | Toda ..................... | B82Y 20/00 |
| | | | 73/105 |
| 6,654,110 B2 * | 11/2003 | Yonezawa ............ | G01N 21/956 |
| | | | 356/237.2 |
| 8,069,008 B2 * | 11/2011 | Kusunose .............. | G01B 11/22 |
| | | | 702/166 |

(Continued)

FOREIGN PATENT DOCUMENTS

| JP | 2006-147848 | 6/2006 |
| JP | 2007-318031 | 6/2007 |

(Continued)

OTHER PUBLICATIONS

Office Action issued on Jul. 29, 2014 on patent application JP2013-261652.

*Primary Examiner* — Roy M Punnoose
(74) *Attorney, Agent, or Firm* — Faegre Baker Daniels LLP

(57) ABSTRACT

Provided are a defect classifying method and an inspection apparatus which are capable of classifying a defect by distinguishing a basal plane dislocation, which is a killer defect in bipolar high-voltage elements, from other defects. The defect classifying method according to the present invention includes: projecting an illumination beam toward a silicon carbide substrate and forming a reflection image and a photoluminescence image; a first inspection step of detecting a defect image from the reflection image formed; a second inspection step of detecting a defect image from the photoluminescence image formed; and a defect classification step of classifying detected defects based on whether or not the defect image is detected and the shape of the detected defect image.

46 Claims, 8 Drawing Sheets

(56) References Cited

U.S. PATENT DOCUMENTS

| | | | |
|---|---|---|---|
| 2002/0162979 A1* | 11/2002 | Kusunose | G01N 21/8901 |
| | | | 250/559.45 |
| 2004/0092042 A1 | 5/2004 | Higgs | |
| 2009/0187378 A1* | 7/2009 | Kusunose | G01B 11/22 |
| | | | 702/166 |
| 2011/0242312 A1* | 10/2011 | Seki | G01N 21/9505 |
| | | | 348/125 |
| 2012/0049085 A1 | 3/2012 | Sappey et al. | |
| 2013/0027543 A1 | 1/2013 | Boeykens et al. | |
| 2013/0242300 A1 | 9/2013 | Sappey | |

FOREIGN PATENT DOCUMENTS

| | | |
|---|---|---|
| JP | 2009-099820 | 7/2009 |
| JP | 2012-174896 | 9/2012 |
| WO | WO 98/11425 | 3/1998 |
| WO | WO 02/077621 | 10/2002 |
| WO | WO 2012/027094 | 3/2012 |

\* cited by examiner

Fig. 8

| | SURFACE INSPECTION | | | PL INSPECTION | | |
|---|---|---|---|---|---|---|
| | REFLECTION | SCATTERING | BAND-EDGE | VISIBLE LIGHT | NIR |
| BPD ※1 | INVISIBLE OR BLACK-DOT | INVISIBLE OR WHITE-DOT | INVISIBLE OR BLACK TRANSVERSE LINE ※2 | INVISIBLE | WHITE TRANSVERSE LINE |
| STACKING FAULT (INSIDE) | INVISIBLE | INVISIBLE | BLACK TRIANGLE OR TRAPEZOID | WHITE TRIANGLE OR TRAPEZOID | BLACK TRIANGLE OR TRAPEZOID |
| STACKING FAULT (SURFACE) | BLACK AND WHITE TRIANGLES OR TRAPEZOIDS | BLACK AND WHITE TRIANGLES OR TRAPEZOIDS | BLACK TRIANGLE OR TRAPEZOID | WHITE TRIANGLE OR TRAPEZOID | BLACK TRIANGLE OR TRAPEZOID |
| TSD/TED ※1 | INVISIBLE OR BLACK AND WHITE DOTS | INVISIBLE OR WHITE DOTS | INVISIBLE OR BLACK DOTS ※2 | INVISIBLE | INVISIBLE OR BLACK DOTS ※2 |

※1 THIS CAN BE VIEWED AS PIT IN EPITAXIAL SURFACE. (THE SHAPE VARIES DEPENDING ON EPITAXIAL CONDITIONS. IT IS ALSO POSSIBLE TO REMOVE SURFACE IRREGULARITIES.)

※2 THIS IS GENERALLY INVISIBLE BUT MAY BE VISIBLE WHEN DOPING CONCENTRATION OF EPITAXIAL LAYER IS EXTREMELY LOW.

DEFECT CLASSIFYING METHOD AND OPTICAL INSPECTION APPARATUS FOR SILICON CARBIDE SUBSTRATE

INCORPORATION BY REFERENCE

This application is based upon and claims the benefit of priority from Japanese patent application No. 2013-261652, filed on Dec. 18, 2013, and Japanese patent application No. 2014-199771, filed on Sep. 30, 2014, the disclosure of which is incorporated herein in its entirety by reference.

BACKGROUND OF THE INVENTION

1. Field of the Invention

The present invention relates to a defect classifying method and an inspection apparatus that detect a defect which is present at a silicon carbide substrate (SiC substrate) and classify the detected defect.

2. Description of Related Art

Silicon carbide has superior physical and thermal properties, and thus is useful for production of a high-voltage, low-loss semiconductor device. In a semiconductor device production process using a SiC substrate, detection of defects which are present at the SiC substrate and classification of the defects which are detected are extremely important with regard to improving the production yield. Especially, in the case of producing a bipolar high-voltage element, a basal plane dislocation (BPD) is a killer defect which has an adverse effect on the performance of the element. For this reason, there is a strong demand for detecting defects by distinguishing the BPD from other defects.

A structure conversion technique for converting basal plane dislocations to threading edge dislocations (LEDs) in the process of forming an epitaxial layer during a SiC substrate production process has been developed. Specifically, in the case where a bipolar device is formed in an area including the BPD, when a current flows in the forward direction, the BPD is changed to a Shockley-type stacking fault, which causes a change in device characteristics and leads to a malfunction. On the other hand, when a bipolar device is formed in a location where the TED is present, the device characteristics are less affected. For this reason, devices that can be put to practical use by using a substrate including the TED can be produced. In addition, the use of the above-mentioned structure conversion technique makes it possible to convert most BPDs existing in the SiC substrate into TEDs. This leads to a further improvement in the production yield of the devices and is extremely useful for the production of high-voltage elements.

On the other hand, the structure conversion from BPDs to TEDs is carried out by appropriately controlling various parameters for metal organic chemical vapor deposition (MOCVD) in the epitaxial layer growth process. To find out the optimum conditions for various parameters in the MOCVD process, it is important to detect BPDs which are present at the SiC substrate on which an epitaxial layer is formed. In other words, if BPDs can be detected at the SiC substrate on which an epitaxial layer is formed, information useful for controlling the MOCVD process can be fed back. Accordingly, in order to improve the efficiency of the conversion from BPDs to TEDs and improve the production yield, it is necessary to develop a defect inspection apparatus capable of selectively detecting defects by distinguishing a basal plane dislocation from other defects.

As an apparatus for inspecting a SiC substrate, an inspection apparatus using a differential interference optical system is known (see, for example, Japanese Unexamined Patent Application Publication No. 2012-174896). In this inspection apparatus, a line-shaped scan beam is projected toward the surface of the SiC substrate through the differential interference optical system and an objective lens. A line sensor receives reflected light reflected on the surface of the SiC substrate. The inspection apparatus that uses the differential interference optical system can detect a change in unevenness of about several nm on the surface of the SiC substrate as a contrast image. This is advantageous in that minute defects can be detected in the image of the surface of the SiC substrate.

As another inspection apparatus, an inspection apparatus that uses a photoluminescence method (PL method) is known (for example, see Japanese Unexamined Patent Application Publication No. 2006-147848). In this known inspection apparatus, ultraviolet light is projected toward a silicon carbide substrate. Further, a photodetector detects photoluminescence light emitted from the silicon carbide substrate through a spectrometer. This known inspection apparatus detects the photoluminescence light, which is advantageous in that a crystal defect existing in the substrate can be detected.

The inspection apparatus that uses the differential interference optical system can detect a minute change in the unevenness on the surface of the substrate as a luminance image. Accordingly, threading screw dislocations and threading edge dislocations, which appear as a pit structure on the surface of the substrate, can be detected. However, the basal plane dislocations hardly appear on the surface of the substrate, or rarely appear as a minute pit structure. Accordingly, the inspection apparatus that uses the differential interference optical system has a drawback that the inspection apparatus cannot clearly detect the basal plane dislocations. On the other hand, in the inspection apparatus that uses the photoluminescence method, a defect existing in the substrate can be detected in a PL image, which is advantageous in that the basal plane dislocations can be clearly detected.

On the PL image, a location where the basal plane dislocation exists is detected as a line-shaped PL image. Accordingly, the basal plane dislocation can be detected in the PL image. However, a carrot defect also exists as a crystal defect specific to the epitaxial layer formed on the SiC substrate. A carrot defect is also a killer defect in the device production process, and thus the carrot defect needs to be detected in the defect inspection process. The PL image of a carrot defect is a line-shaped image which is similar to that of the basal plane dislocation. Accordingly, the carrot defect can be detected by a photoluminescence light inspection. However, the cause of occurrence of the carrot defect and the measures to prevent the occurrence of the carrot defect are different from those of the BPD. Therefore, there is a strong demand for detecting the BPD and the carrot defect by distinguishing them from each other. However, since both the PL image of the BPD and the carrot defect are line-shaped images, it is actually difficult to detect the BPD and the carrot defect by distinguishing them from each other in the photoluminescence light inspection.

There is also a strong demand for further increasing the accuracy of classifying detected defects in order to improve the production yield in the device production process using the SiC substrate. In other words, if the accuracy of classifying defects can be further improved, information useful for the epitaxial layer growth process can be fed back. Accordingly, in order to improve the production yield of devices that uses silicon carbide, it is also important to further improve the accuracy of classifying defects.

An object of the present invention is to realize a defect classifying method and an inspection apparatus which are capable of classifying defects by distinguishing a basal plane dislocation, which is a killer defect in bipolar high-voltage elements, from other defects. Another object of the present invention is to realize a defect classifying method and device capable of classifying defects, which are present at a SiC substrate, with high accuracy.

SUMMARY OF THE INVENTION

A first exemplary aspect of the present invention is a defect classifying method that detects a defect which is present at a silicon carbide substrate or a silicon carbide substrate having an epitaxial layer formed thereon, and classifies the defect by distinguishing a basal plane dislocation from other crystal defects, the defect classifying method including: projecting illumination light of an ultraviolet region toward the silicon carbide substrate and scanning the silicon carbide substrate with the illumination light of the ultraviolet region; condensing reflected light and photoluminescence light emitted from the silicon carbide substrate; separating, from the condensed light, each of the reflected light and the photoluminescence light, and detecting each of the separated reflected light and the separated photoluminescence light; a first defect inspection step of detecting a defect from the detected reflected light to perform defect detection using the reflected light; a second defect inspection step of detecting a defect from the detected photoluminescence light to perform defect detection using the photoluminescence light; and a defect classification step of classifying each defect detected in the first and second defect inspection steps. Defect detection using the reflected light and defect detection using the photoluminescence light are performed in parallel. In the defect classification step, the basal plane dislocation is distinguished by using both a result of the defect detection using the reflected light and a result of the defect detection using the photoluminescence light.

The present inventors captured the reflection image of each silicon carbide substrate having an epitaxial layer formed thereon, by using an inspection apparatus including a differential interference optical system, and obtained the following experimental results. In the samples including a basal plane dislocation, no defect image was detected in most silicon carbide substrates, while a contrast image in which a minute bright image portion and a minute dark image portion were connected was detected in some samples. The results show that the basal plane dislocation hardly appears on the surface of the epitaxial layer, but is present in the epitaxial layer. On the other hand, in the case of samples including a carrot defect, a line-shaped or carrot-shaped defect image was detected. Accordingly, the carrot defect appears as a line-shaped protrusion on the surface of the epitaxial layer. In the samples including a threading screw dislocation and a threading edge dislocation, a spot-shaped contrast defect image in which a bright image portion and a dark image portion were connected was detected. Accordingly, the threading screw dislocation defect and the threading edge dislocation defect appear as a pit structure on the surface of the epitaxial layer. Further, in the samples including a micropipe defect, a defect image of a spot-shaped low-luminance image was detected. In other words, since the micropipe defect is a defect in the form of a through-hole, no reflected light is generated and the defect is detected as a spot-shaped low-luminance image. Furthermore, in the samples including a stacking fault, a triangular high-luminance image, or two line-shaped defect images crossing each other were detected.

The present inventors conducted a defect inspection using photoluminescence light on the samples used for the above experiment, and obtained the following experimental results. In the inspection using photoluminescence light having a wavelength region of 700 nm or more, a line-shaped photoluminescence image extending in the step-flow direction was detected in the samples including a basal plane dislocation and samples including a carrot defect. In the samples including a threading screw dislocation and a threading edge dislocation and the sample including a micropipe defect, no photoluminescence image was detected. Further, in the inspection using a band-edge emission wavelength (380 nm) of a 4H-silicon carbide substrate, no defect image was detected in the samples including a basal plane dislocation and a carrot defect. On the other hand, in the samples including a stacking fault, a block-shaped low-luminance image having a triangular or trapezoidal shape, for example, was detected. In the samples including a threading screw dislocation, a threading edge dislocation, and a micropipe defect, a spot-shaped low-luminance image was detected.

The defects can be classified based on the above experimental results. Specifically, both a reflected light inspection and a photoluminescence light inspection are performed on the silicon carbide substrate on which the epitaxial layer is formed, to thereby obtain information indicating whether or not a defect image is detected and information indicating the shape of the detected defect image. The use of the information indicating whether or not a defect image is detected and the information indicating the shape of the defect image makes it possible to classify the defects specific to the silicon carbide substrate on which the epitaxial layer is formed. When a line-shaped defect image is detected in the inspection using photoluminescence light of a visible region or an infrared region and when no defect image is detected or a pit-shaped defect image is detected in the inspection using the reflected light, the detected defect can be classified as a basal plane dislocation. When a line-shaped defect image is detected in both the inspection using the photoluminescence light of the visible region or the infrared region and the inspection using the reflected light, the detected defect can be classified as a carrot defect. When a contrast defect image is detected in the inspection using the reflected light and when no defect image is detected in the inspection using the photoluminescence light of the visible region or the infrared region, the detected defect can be classified as a threading screw dislocation defect or a threading edge dislocation defect. When a spot-shaped low-luminance image is detected in the inspection using the reflected light and when a spot-shaped low-luminance image is detected in the inspection using the band-edge emission wavelength, the detected defect can be determined to be a micropipe defect. When a block-shaped low-luminance defect image having a triangular or trapezoidal shape, for example, is detected in the inspection using the band-edge emission wavelength of 380 nm, the detected defect can be determined to be a stacking fault.

Accordingly, the basal plane dislocation, which is a killer defect in bipolar devices, can be detected and distinguished from other defects by performing both the reflected light inspection and the photoluminescence light inspection. Further, another killed defect, i.e., a carrot defect, can be detected and distinguished from other defects by performing both the reflected light inspection and the photoluminescence light inspection. Furthermore, a threading screw dislocation, a threading edge dislocation, and a micropipe defect can also be detected and distinguished from other crystal defects. Moreover, the inspection using the band-edge emission wavelength of 380 nm makes it possible to detect a stacking fault by distinguishing it from other defects.

A second exemplary aspect of the present invention is a defect classifying method that detects a defect which is present at a silicon carbide substrate or a silicon carbide substrate having an epitaxial layer formed thereon, and classifies the defect by distinguishing a basal plane dislocation from other crystal defects, the defect classifying method including: projecting illumination light of an ultraviolet region toward the silicon carbide substrate and scanning the silicon carbide substrate with the illumination light; condensing scattered light and photoluminescence light emitted from the silicon carbide substrate; separating, from the condensed light, each of the scattered light and the photoluminescence light, and detecting each of the scattered light and the photoluminescence light; a first defect inspection step of detecting a defect from the detected scattered light; a second defect inspection step of detecting a defect from the detected photoluminescence light; and a defect classification step of classifying each defect detected in the first and second defect inspection steps. Defect detection using the scattered light and defect detection using the photoluminescence light are performed in parallel. In the defect classification step, the basal plane dislocation is distinguished by using both a result of the defect detection using the scattered light and a result of the defect detection using the photoluminescence light As with the reflection image, a scattered light image is an image formed by the reflected light emitted from the surface of the substrate. Accordingly, the scattered light image can be used instead of the reflection image, and the defect can be classified using a defect image detected in the scattered light image and a defect image detected in the photoluminescence image.

A third exemplary aspect of the present invention is a defect classifying method that detects a defect which is present at a silicon carbide substrate or a silicon carbide substrate having an epitaxial layer formed thereon, and classifies the detected defect, the defect classifying method comprising: projecting illumination light of an ultraviolet region toward the silicon carbide substrate and scanning the silicon carbide substrate with the illumination light; condensing reflected light and photoluminescence light emitted from the silicon carbide substrate; detecting, from the condensed light, reflected light, photoluminescence light of a first wavelength region including a band-edge emission wavelength of silicon carbide, and photoluminescence light of a second wavelength region having a wavelength longer than that of the first wavelength region; a first defect inspection step of detecting a defect from the detected reflected light; a second defect inspection step of detecting a defect from the detected photoluminescence light of the first wavelength region; a third defect inspection step of detecting a defect from the detected photoluminescence light of the second wavelength region; and a defect classification step of classifying each defect detected in the first to third defect inspection steps. In the defect classification step, the basal plane dislocation is distinguished by using both a result of the defect detection using the reflected light and a result of the defect detection using the photoluminescence light of the second wavelength region.

In the photoluminescence light inspection, if a photoluminescence image having a wavelength equal to the band-edge emission wavelength of 380 nm and a photoluminescence image having a wavelength of 700 nm or more are detected, both a photoluminescence image resulting from a basal plane dislocation and a carrot defect and a photoluminescence image resulting from a stacking fault can be detected.

A fourth exemplary aspect of the present invention is an inspection apparatus that detects a defect which is present at a silicon carbide substrate or a silicon carbide substrate having an epitaxial layer formed thereon, and classifies the defect by distinguishing a basal plane dislocation from other crystal defects, the inspection apparatus including: an illumination unit that projects illumination light of an ultraviolet region toward the silicon carbide substrate; a scanner that scans a surface of the silicon carbide substrate with the illumination light; an objective lens that condenses reflected light and photoluminescence light emitted from the silicon carbide substrate; a separation unit that separates each of the reflected light and the photoluminescence light from the light condensed by the objective lens; first and second photodetectors that respectively detect the separated reflected light and the separated photoluminescence light; and a signal processor that detects a defect based on output signals output from the first and second photodetectors and classifies the detected defect. The signal processor includes: a first defect detection unit that detects a defect from the output signal output from the first photodetector; a second defect detection unit that detects a defect from the output signal output from the second photodetector; and a defect classification unit that classifies each defect detected by the first and second defect detection units. The defect classification means distinguishes the basal plane dislocation by using both a result of the defect detection using the reflected light and a result of the defect detection using the photoluminescence light.

In a preferred embodiment of the inspection apparatus according to the present invention, the signal processor further includes: a unit that creates defect data including address information indicating a shape and a position of a defect image detected by the first and second defect detection units; and a defect memory that stores the created defect data. The defect classification unit receives information including an address of a defect as defect information to be classified. Upon receiving the defect information to be classified, the defect classification unit accesses the defect memory and classifies the defect based on the presence or absence of a defect image at the address included in the received defect information and the shape of the defect image.

Since the defect image of the reflection image and the defect image of the photoluminescence image are individually formed, it is necessary to provide a unit that associates the defect images with each other. Accordingly, in the present invention, the defect image of the reflection image and the defect image of the photoluminescence image are associated with each other by using the address information indicating the position of each defect image. Further, information including the address of each defect is used as the defect information to be classified. This configuration makes it possible to classify the defect based on the presence or absence of a defect image at a defect site, which is designated by the address information indicating the position of the defect, and based on the shape of the defect image.

According to the present invention, a change in minute unevenness of the surface of the epitaxial layer formed on the silicon carbide substrate is detected in the reflection image, and a change in the crystal structure within the epitaxial layer is detected in the photoluminescence image. This makes it possible to simultaneously detect both a defect appearing on the surface of the substrate and a defect existing only in the substrate. As a result, defects can be classified based on a lot of defect information, leading to a further improvement in the classification accuracy.

The basal plane dislocation hardly appears in the reflection image, but appears as a line-shaped image in the photoluminescence image. This feature is different from the feature of a stacking fault or a carrot defect. Accordingly, the basal plane dislocation can be classified and distinguished from other defects by scanning the silicon carbide substrate once with an illumination beam and detecting both the reflected light and the photoluminescence light in parallel.

The above and other objects, features and advantages of the present invention will become more fully understood from the detailed description given hereinbelow and the accompanying drawings which are given by way of illustration only, and thus are not to be considered as limiting the present invention.

BRIEF DESCRIPTION OF THE DRAWINGS

FIG. 8 is a table showing the inspection results and the correspondence among the defects to be distinguished from each other.

DESCRIPTION OF THE EXEMPLARY EMBODIMENTS

Figure 1:
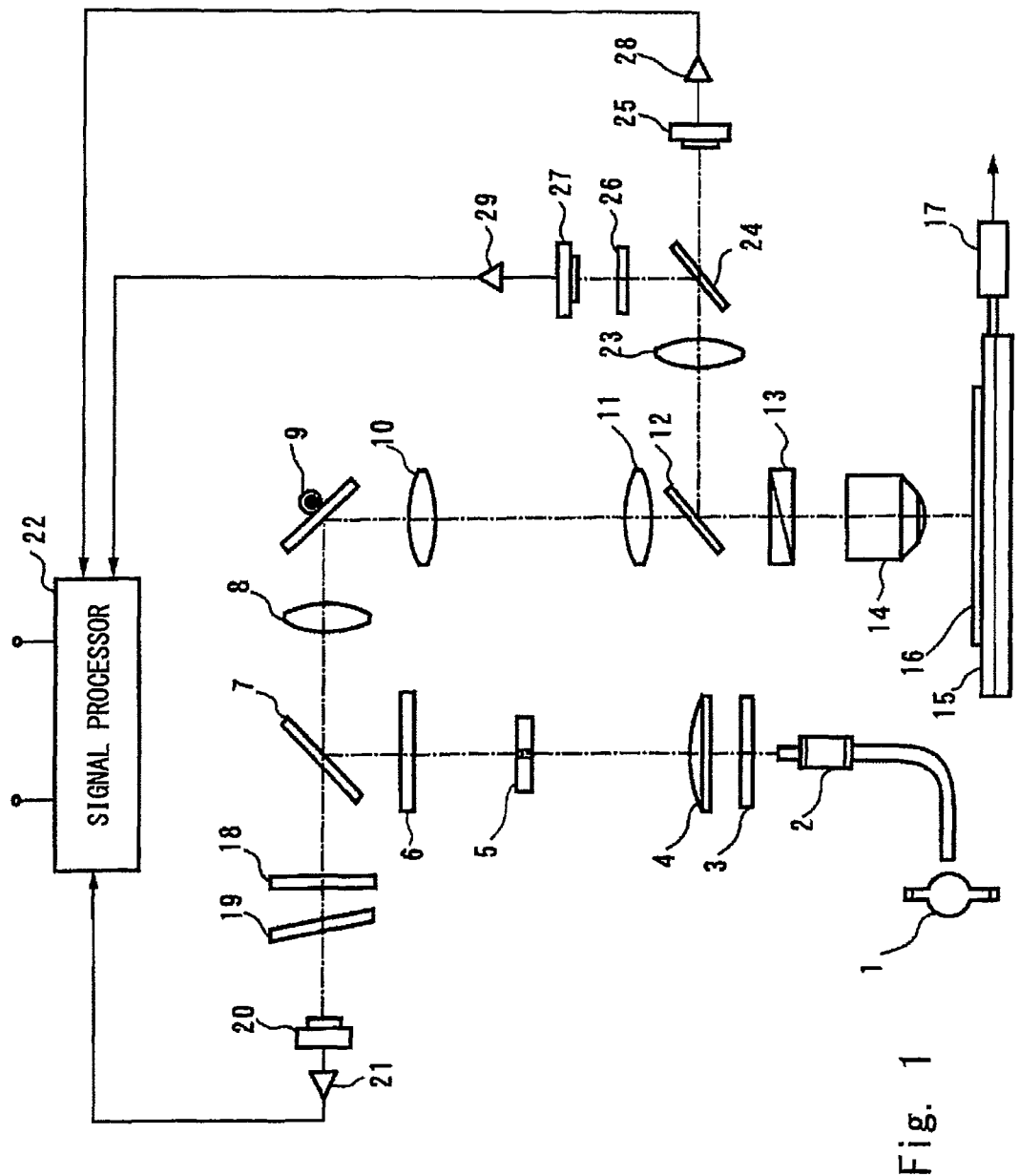
FIG. 1 is a diagram showing an example of an inspection apparatus that carries out a defect classifying method according to the present invention.

FIG. 1 is a diagram showing an example of an inspection apparatus that carries out a defect classifying method according to the present invention. In this example, the entire surface of a silicon carbide substrate to be inspected is scanned by using a confocal scanning device including a differential interference optical system. Reflected light and photoluminescence light, which are emitted from the substrate, are individually detected, and a reflected light inspection and a photoluminescence light inspection are carried out in parallel. A silicon carbide substrate on which an epitaxial layer is formed is used as the silicon carbide substrate to be inspected. The inspection apparatus detects and classifies defects formed in the epitaxial layer. A silicon carbide substrate having no epitaxial layer formed thereon can also be used as the silicon carbide substrate to be inspected.

Referring to FIG. 1, an illumination light source 1 that produces an illumination beam is a light source that emits ultraviolet light that generates photoluminescence light when the illumination beam is projected toward the silicon carbide substrate. In other words, a light source having energy larger than the band-gap energy of silicon carbide is used. For example, a He—Cd laser that emits laser light having a wavelength of 320 nm, the fourth-harmonic of a YAG laser that produces a laser beam having a wavelength of 266 nm, and a mercury-xenon lamp can be used. In this example, a mercury-xenon lamp is used as the illumination light source and light having a wavelength of 313 nm is used as the illumination beam.

The illumination beam emitted from the illumination light source 1 is directed onto an optical fiber bundle 2 which includes a plurality of optical fibers stacked in a cylindrical shape. The optical fiber bundle 2 is a bundle of a plurality of optical fibers. The illumination beam propagates through each optical fiber and is output as a divergent beam having a circular shape in cross-section. The illumination beam from the optical fiber bundle 2 is directed onto a filter 3. The filter 3 is, for example, a band-pass filter. The filter 3 emits an illumination beam having a wavelength of 313 nm.

The illumination beam emitted from the filter 3 is converted into parallel beams by a converging lens 4, and the parallel beams are directed onto a slit 5. The slit 5 is placed at a pupil location of the converging lens 4. The slit 5 has an elongated opening extending in a first direction (a direction perpendicular to the drawing sheet). The first direction is herein referred to as an X-direction. The width of the opening of the slit 5 is set to, for example, 10 to 20 μm. Accordingly, an elongated line-shaped light beam extending in the first direction is emitted from the slit 5. The line-shaped light beam emitted from the slit 5 is directed onto a polarizer 6. The polarizer 6 converts the light beam into a polarized light beam having a single vibration plane. This line-shaped polarized light beam is reflected by a half-mirror 7 and is directed onto a lens 8. The half-mirror 7 functions as a beam splitter. The lens 8 is a relay lens. The polarized light beam is directed onto a vibrating mirror 9 through the lens 8. The vibrating mirror 9 functions as a beam scanning device.

In the case of reviewing the image of the surface of the silicon carbide substrate, the vibrating mirror 9 deflects the illumination beam in a second direction (Y-direction) perpendicular to the first direction. During an inspection, the entire surface of the substrate is scanned by a two-dimensional movement of a stage that supports a sample. Accordingly, the vibrating mirror 9 functions as a total reflection mirror during the inspection. The line-shaped light beam emitted from the vibrating mirror 9 is directed onto a first dichroic mirror 12 through a first relay lens 10 and a second relay lens 11. The first dichroic mirror 12 has a function of separating reflected light and photoluminescence light which are emitted from the silicon carbide substrate. For example, the first dichroic mirror 12 reflects light having a wavelength of 370 nm or more and transmits light having a wavelength of 370 nm or less. The illumination beam transmitted through the first dichroic mirror 12 is directed onto a Nomarski prism 13. In this example, a Nomarski prism is used as the differential interference optical system. The line-shaped illumination beam incident on the Nomarski prism 13 is converted into two sub-beams having vibration planes perpendicular to each other. A phase difference of $(2m+1)\pi/2$ (m is a natural number) is introduced between the two sub-beams. Accordingly, a defect formed on the surface of a silicon carbide substrate 16 and having a change in height of several nm can be detected as a contrast luminance image. The shearing amount of the Nomarski prism is set to, for example, 2 μm. The Nomarski prism 13 is removably disposed on an optical path. The Nomarski prism 13 is inserted in the optical path in the case of capturing a confocal differential interference image of the silicon carbide substrate 16. In the case of capturing images other than the confocal differential interference image, the Nomarski prism 13 is removed from the optical path. For example, in the case of capturing a three-dimensional confocal image of a sample and capturing a surface contour image of the sample, the Nomarski prism 13 is removed from the optical path.

The two sub-beams emitted from the Nomarski prism 13 are directed onto an objective lens 14. The objective lens 14 condenses the incident two line-shaped sub-beams and projects the beams toward the silicon carbide substrate 16 which is placed on a stage 15. In this example, the silicon carbide substrate (SiC substrate) 16 on which an epitaxial layer is formed is used as a substrate to be inspected. The inspection apparatus detects a defect existing in the epitaxial layer. The stage 15 is composed of an XY stage. The positional information of the stage 15 is detected by a position sensor 17. The position sensor 17 supplies a signal processor with the positional information of the stage 15. During the inspection, the stage 15 moves in a zig-zag manner in the Y-direction and the X-direction, and the entire surface of the silicon carbide substrate 16 is scanned with the illumination beam. In the case of reviewing a detected defect by using the address of the detected defect, the stage 15 is allowed to move in the X-direction and the Y-direction based on the coordinate information of the defect so as to position the defect within the field of view. Confocal differential interference images of the defect and the vicinity of the defect can be captured by scanning the vibrating mirror 9 in the second direction (Y-direction).

When the illumination beam having a wavelength of 313 nm is directed onto the silicon carbide substrate 16, a part of the illumination beam is reflected by the surface of the substrate and forms a reflected beam. The remainder of the illumination beam enters the silicon carbide substrate and generates photoluminescence light when a defect exists in the substrate.

When the defect appears as an unevenness of about several nm to several hundred nm on the surface of the substrate, a phase difference corresponding to a change in the height of the defect is introduced between the two sub-beams reflected on the surface of the substrate. As a result, two reflected sub-beams including phase difference information corresponding to the height of the defect existing on the surface of the substrate are formed. These two reflected sub-beams are condensed by the objective lens 14 and are directed onto the Nomarski prism 13. The beams are combined by the Nomarski prism 13, with the result that an interference beam including the phase difference information indicating a change in the height of the silicon carbide substrate 16 is formed. For example, when a concave or convex defect of about several nm exists on the surface of the silicon carbide substrate 16, one of the two sub-beams incident on the surface of the SiC substrate scans the defect, and the other sub-beam scans the normal surface portion. Accordingly, a phase difference corresponding to the height of the defect is introduced between the two sub-beams. As a result, the defect appearing on the surface of the substrate is detected as a luminance image.

When a crystal defect exists in the epitaxial layer of the silicon carbide substrate, the illumination beam which has been transmitted through the surface of the substrate and entered the substrate is directed onto the defect. When ultraviolet light is directed onto the defect, photoluminescence light having various wavelengths and forms is generated depending on the type of the defect. In the case of a basal plane dislocation defect and a carrot defect, photoluminescence light having a wavelength region of 700 nm to 1100 nm is generated. In the case of a threading screw dislocation defect and a threading edge dislocation defect, photoluminescence light of the visible region and the infrared region is not generated. In the band-edge emission wavelength of 4H—SiC, light emission is detected in a high-quality area with no defect, while in a location where a stacking fault exists, light emission is less likely to be detected and a dark block-shaped defect image is detected.

The reflected light and photoluminescence light emitted from the silicon carbide substrate 16 are condensed by the objective lens 14, are transmitted through the Nomarski prism 13, and are directed onto the first dichroic mirror 12. The first dichroic mirror 12 transmits light having a wavelength of 370 nm or less and reflects light having a wavelength of more than 370 nm. Accordingly, the photoluminescence light generated due to a basal plane dislocation, a stacking fault, and a carrot defect is reflected by the first dichroic mirror 12. On the other hand, the reflected light reflected on the surface of the silicon carbide substrate 16 is transmitted through the first dichroic mirror 12.

The reflected light transmitted through the first dichroic mirror 12 passes through the second relay lens 11 and the first relay lens 10. The reflected light which has passed through the first relay lens 10 is reflected by the vibrating mirror 9 and is directed onto the lens 8. This lens 8 operates as an imaging lens with respect to the reflected light from the silicon carbide substrate 16. The reflected light which has passed through the lens 8 is transmitted through the half-mirror 7. The reflected light transmitted through the half-mirror 7 is directed onto a first photodetector 20 through an analyzer 18 and a positioner 19. In this example, the first photodetector 20 is composed of a line sensor serving as an imaging device. An image signal output from the first photodetector 20 is supplied to a signal processor 22 through an amplifier 21.

The photoluminescence light reflected by the first dichroic mirror 12 is directed onto a second dichroic mirror 24 through an imaging lens 23. The second dichroic mirror 24 separates the photoluminescence light of the infrared region and the visible region from the band-edge emission in the vicinity of 380 nm. For example, the second dichroic mirror 24 transmits light having a wavelength of 700 nm or more and reflects light having a wavelength of 700 nm or less. Accordingly, the photoluminescence light generated due to a basal plane dislocation and a carrot defect is transmitted through the second dichroic mirror 24 and is directed onto a second photodetector 25. The photoluminescence light generated due to the band-edge emission is reflected by the second dichroic mirror 24. The photoluminescence light reflected by the second dichroic mirror 24 is directed onto a third photodetector 27 through a band-pass filter 26. The band-pass filter 26 transmits light having a wavelength in the range of 380 nm±5 nm.

The second photodetector 25 and the third photodetector 27 are line sensors. An image signal output from the second photodetector 25 is supplied to the signal processor 22 through an amplifier 28. An image signal output from the third photodetector 27 is supplied to the signal processor 22 through an amplifier 29.

Figure 2:
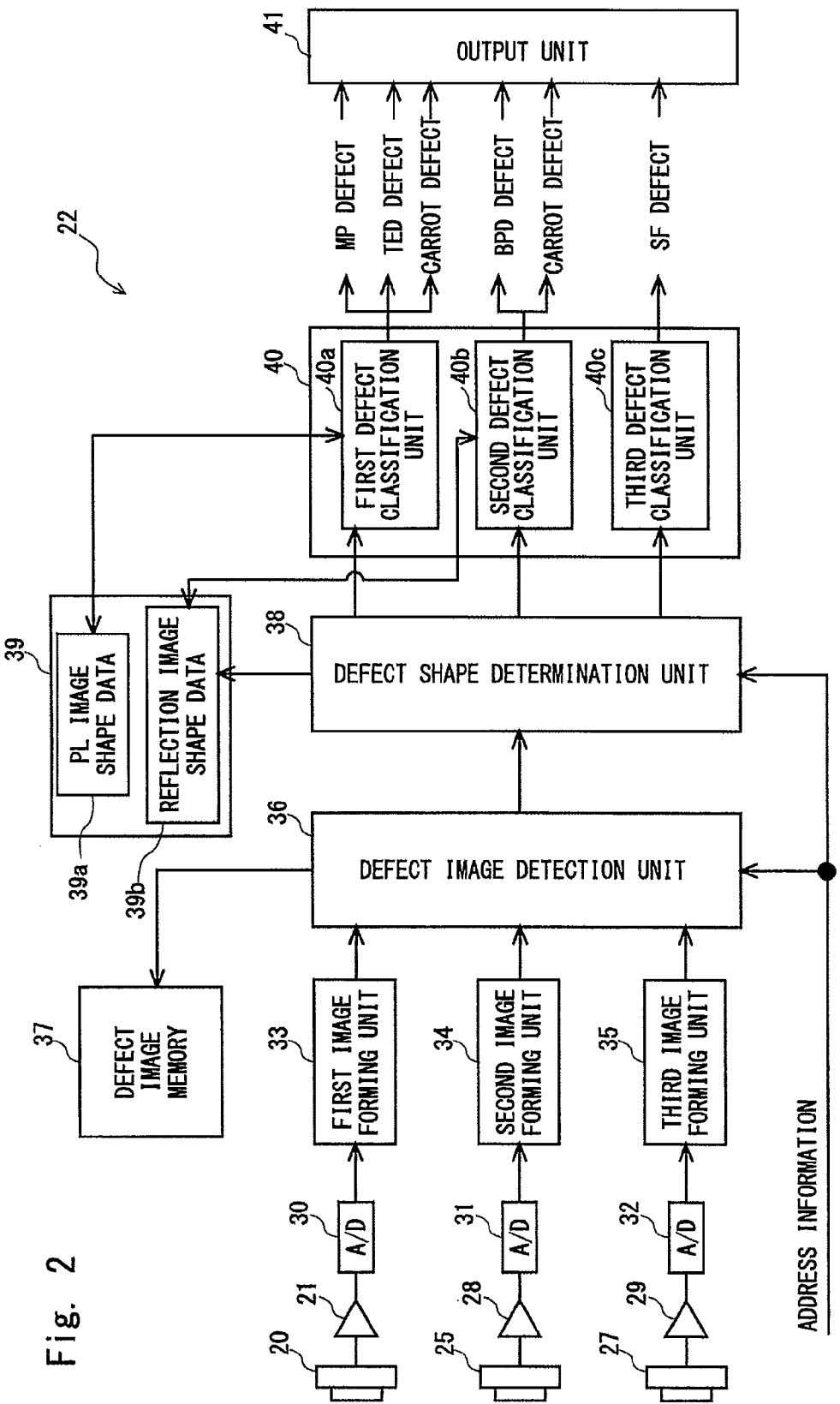
FIG. 2 is a diagram showing an example of a signal processor according to the present invention.

FIG. 2 is a diagram showing an example of the signal processor 22. The signal processor 22 includes, for example, a computer including a processor and a memory. The processor executes a program stored in the memory or the like, to thereby execute a process for distinguishing a defect as described below. In this example, the inspection apparatus executes the detection of a defect by a reflected light inspection and the detection of a defect by a photoluminescence light inspection in parallel. The signal processor 22 classifies the detected defect based on the inspection results. The first to third photodetectors 20, 25, and 27 output image signals to A/D converters 30 to 32 through the amplifiers 21, 28, and 29, respectively. The A/D converters 30 to 32 respectively covert the image signals into digital signals. The A/D converter 30 performs AD conversion of a first image signal from the first photodetector 20, and outputs the converted first image signal to a first image forming unit 33. The A/D converter 31 performs AD conversion of a second image signal from the second photodetector 25, and outputs the converted second image signal to a second image forming unit 34. The A/D converter 32 performs AD conversion of a third image signal from the third photodetector 27, and outputs the converted third image signal to a third image forming unit 35.

The image signal output from the first photodetector 20 is supplied to the first image forming unit 33. The first image forming unit 33 forms a two-dimensional image (reflection image) of the reflected light based on the image signal from the first photodetector 20. The second image signal output from the second photodetector 25 is supplied to the second image forming unit 34. The second image forming unit 34 forms a two-dimensional image (first photoluminescence image) of the photoluminescence light having a wavelength of 700 nm or more based on the image signal from the second photodetector 25. The third image signal output from the third photodetector 27 is supplied to the third image forming unit 35. The third image forming unit 35 forms a two-dimensional image (second photoluminescence image) on the photoluminescence light having a center wavelength of 380 nm based on the third image signal from the third photodetector 27.

The reflection image signal, the first photoluminescence image signal, and the second photoluminescence image signal are supplied to a defect image detection unit 36. The defect image detection unit 36 compares, for each pixel, the received reflection image signal, first photoluminescence image signal, and second photoluminescence image signal with a reference luminance value. Further, the defect image detection unit 36 detects pixels each indicating a luminance value outside the range of the reference luminance value, and forms a defect image. For example, in the detection of a defect image in the reflection image, the defect image is formed by mapping the pixels each indicating a value outside the range of the reference luminance value. The defect which has a luminance lower than a lower reference luminance value of the range is a low luminance defect. The defect which has a luminance higher than an upper reference luminance value of the range is a higher luminance defect. In the photoluminescence image inspection, a defect image is detected by mapping the pixels in which an image signal having a luminance exceeding a reference value is detected. Alternatively, in the detection of a defect image in the PL image, the defect image is formed by mapping the pixels each indicating a value outside the range of the reference luminance value. The defect which has a luminance lower than a lower reference luminance value of the range is a low luminance defect. The defect which has a luminance higher than an upper reference luminance value of the range is a high luminance defect.

The defect image detection unit 36 is also supplied with address information indicating a location where the illumination beam is directed onto the silicon carbide substrate 16. This address information is generated based on the positional information of the stage 15 that supports the silicon carbide substrate 16 and the pixel information on each of the first to third line sensors. The detected defect image and the address information are stored in a defect image memory 37. After the inspection of the entire surface of the substrate is finished, an operator can display and observe a desired defect image on a monitor by accessing the defect image memory 37 by using the address of the defect.

The detected defect image is supplied to a defect shape determination unit 38. The defect shape determination unit 38 determines the shapes of the detected defect image of the reflection image and the detected defect image of each of the first and second photoluminescence images. Specifically, as for the shape of the defect image of the reflective image, the shapes of input defect images are classified into a spot-shaped low-luminance image, a spot-shaped contrast luminance image, a line-shaped image, and other images. As for the shape of the defect image of the first photoluminescence image, the input defect images are classified into a line-shaped image and other images. As for the shape of the defect image of the second photoluminescence image, the input defect images are classified into a spot-shaped low-luminance image, a block-shaped low-luminance image, and other images. The defect shape determination unit 38 also determines the size of each defect image. Further, the address information indicating the location where the illumination beam is directed onto the silicon carbide substrate 16 is supplied to the defect shape determination unit 38. Then the defect shape determination unit 38 creates defect data information including shape information, size information, and address information on the detected defect image, and writes the created defect data information into a defect data memory 39. The above-described method for classifying the shapes of defect images is illustrated by way of example. The defect images can be classified into various defect shapes depending on the object of the inspection and the defect type.

The defect data memory 39 includes two storage areas, i.e., a first storage area 39a and a second storage area 39b. The first storage area 39a stores defect data including the shape, characteristics, size, and address of each defect image detected in the photoluminescence image inspection. The second storage area 39b stores defect data including the shape, characteristics, size, and address of each defect image detected in the reflection image inspection.

The created defect data is supplied to a defect classification unit 40 as defect information to be classified. The defect classification unit 40 includes a first classification unit 40a, a second classification unit 40b, and a third classification unit 40c. The first classification unit 40a classifies the defect images detected in the reflection image inspection. The second classification unit 40b classifies the defect images detected in the first photoluminescence image inspection. The third classification unit 40c classifies the defect images detected in the second photoluminescence image inspection.

Upon receiving the defect information to be classified, the first classification unit 40a accesses the first storage area 39a of the defect data memory 39 in which the photoluminescence image shape data (PL image shape data) is stored. The first classification unit 40a acquires defect shape data on the photoluminescence image having the same address as that included in the received defect information. The first classification unit 40a compares the received defect data on the reflection image with the acquired defect shape data on the photoluminescence image, and classifies the defect. For example, when a spot-shaped low-luminance image is received as the defective shape data on the reflection image and when the spot-shaped low-luminescence image at the band-edge emission wavelength exists at the address corresponding to the PL image, the first classification unit 40a determines that the received defect shape data indicates a micropipe defect (MP defect). Further, when the received defect data on the reflection image indicates a contrast luminance image and when no defect image exists at the address corresponding to the PL image, the first classification unit 40a determines that the received defect shape data indicates a threading edge dislocation (TED) or a threading screw dislocation (TSD). When the received defect data on the reflection image indicates a contrast luminance image and when a spot-shaped low-luminance image having a band-edge emission wavelength exists at the address corresponding to the PL image, the first classification unit 40a determines that the received defect shape data indicates a threading edge dislocation (TED) or a threading screw dislocation (TSD). Further, when the received defect shape data indicates a line-shaped defect image and when the defect shape data at the address corresponding to the PL image indicates a line-shaped image, the defect in the shape data is classified as a carrot defect.

Upon receiving the defect information to be classified, the second classification unit 40b access the second storage area 39b of the defect data memory 39. The second classification unit 40b acquires defect shape data on the reflection image having an address included in the received defect information. The second classification unit 40b compares the received defect shape data on the photoluminescence image with the defect shape data on the reflection image acquired from the defect data memory, and classifies the defect. For example, when a line-shaped image is received as the defect shape data on the photoluminescence image and when no defect shape data exists at the address corresponding to the reflection image, the second classification unit 40b classifies the received defect shape data as a basal plane dislocation (BPD). When a line-shaped image is received as the defect shape data on the photoluminescence image and when the defect shape data on a contrast image indicating a pit structure exits at the address corresponding to the reflection image, the second classification unit 40b classifies the received defect shape data as a basal plane dislocation (BPD). When a line-shaped image is received as the defect shape data on the photoluminescence image and when the line-shaped image exists at the address corresponding to the reflection image, the second classification unit 40b determines the received defect shape data as a carrot defect.

The third classification unit 40c receives a block-shaped low-luminance image and a spot-shaped low-luminance image as defect images. The block-shaped low-luminance image has no particular relevance to the shape of the defect image of the reflection image. Accordingly, the third classification unit 40c determines the defect as a stacking fault (SF) without accessing the defect data memory. The spot-shaped low-luminance image, which is classified in the reflection image inspection, is not classified in the third classification unit 40c and passes therethrough.

Alternatively, the third classification unit 40c determines the defect as a stacking fault (SF) when the defect image detection unit 36 detects the high luminance defect in the PL image of the visible light formed by the second image forming unit 33 and detects the low luminance defect in the PL image formed by the third image forming unit 35. That is, when the high luminance defect is detected with the PL light of the visible light in the second inspection and when the low luminance defect is detected with the photoluminecense light of near infrared light (NIR) in the third inspection, the third classification unit 40c determines the defect as a stacking fault (SF). The photoluminecense of the near infrared light may have a wavelength different from that of the band edge emission. The band pass filters, the dichroic mirrors and so on can be adequately used based on the wavelength of the light to be detected. For example, the dichroic mirror 24 can separate the visible light from the infrared light. The dichoic mirror 24 transmits the visible light and reflects the near infrared light. The band pass filter 26 transmits the infrared light which is reflected by the dichroic mirror 24.

The classified defect classification information and the address information are supplied to an output unit 41. The operator inputs designation information, which specifies the type and the mode of occurrence of a desired defect, through an input device, such as a keyboard. For example, when the density of occurrence of basal plane dislocations is designated, the output unit 41 calculates the number or the density of basal plane dislocations per unit area and outputs the calculation result. Alternatively, the main surface of the silicon carbide substrate 16 can be divided into chip areas in which chips are to be formed, and defect information indicating the number of detected basal plane dislocations in each chip area can be output. Further, when the type and the number of detected defects in each chip area are designated in the designation information, the output unit 41 can output, for each chip area, defect information indicating the type and the number of defects existing in each chip area. The output unit 41 is, for example, a monitor or a printer.

The basal plane dislocation (BPD), the threading edge dislocation (TED) and the heading screw dislocation (TSD) are defects as described below.

Basal Plane Dislocation (BPD)

Specifically, the basal plane dislocation literally refers to a dislocation existing in the (0001) plane (c-plane), which is a basal plane of a SiC monocrystal. In a broader sense, there are various types of basal plane dislocations including a perfect dislocation with Burger's vector $b=<11-20>/3$, a partial dislocation of a Frank fault in which the c-component is included in "b", and a partial dislocation existing at the boundary between a stacking fault and a perfect crystal. When the dislocation is simply called a basal plane dislocation, it indicates a dislocation with Burger's vector $b=<11-20>/3$ in most cases. When a current is caused to flow in the forward direction in a bipolar device, the basal plane dislocation with Burger's vector $b=<11-20>/3$ is expanded while a Shockley-type stacking fault is formed. This results in deterioration of the forward characteristic of the device. Therefore, the technique for converting such a basal plane dislocation into a threading edge dislocation, which has less adverse effect on the device and has the same Burger's vector as that of the basal plane dislocation, is extremely important.

Threading Edge Dislocation (TED)

Specifically, the edge dislocation is a crystal defect in which the Burger's vector (b), which represents the displacement direction of a crystal, and the dislocation line are perpendicular to each other. The crystal defect has such a shape that an edge-shaped extra atomic plane is introduced in perfect crystal planes. In the case of a hexagonal crystal, the edge dislocation in which the dislocation line threads through the c-plane is referred to as a threading edge dislocation. The direction of the dislocation line is parallel to the c-axis, and the Burger's vector is expressed as $b=<11-20>/3$. The threading edge dislocation and the basal plane dislocation having the same Burger's vector as that of the threading edge dislocation can be mutually converted.

Threading Screw Dislocation (TSD)

Specifically, the screw dislocation is a crystal defect in which the Burger's vector (b), which represents the displacement direction of a crystal, and the dislocation line are parallel to each other, and atomic planes are disposed in a spiral manner around the dislocation line. In the case of a hexagonal crystal, the screw dislocation in which the dislocation line threads through the c-plane is referred to as a threading screw dislocation. The direction of the dislocation line is parallel to the c-axis, and the Burger's vector is expressed as b=<0001> and is parallel to the dislocation line.

The threading screw dislocation having a large Burger's vector becomes a micropipe. In the 4H polytype of a SiC monocrystal, when the magnitude of the Burger's vector is more than three times the size of a unit cell in the c-axis direction, the dislocation is considered to become a micropipe.

Note that a threading mixed dislocation (b=<0001>+<11-20>/3) also exits in the SiC. However, since it is difficult to distinguish the threading screw dislocation from the threading mixed dislocation, they are generally referred to collectively as the threading screw dislocation.

Figure 3:
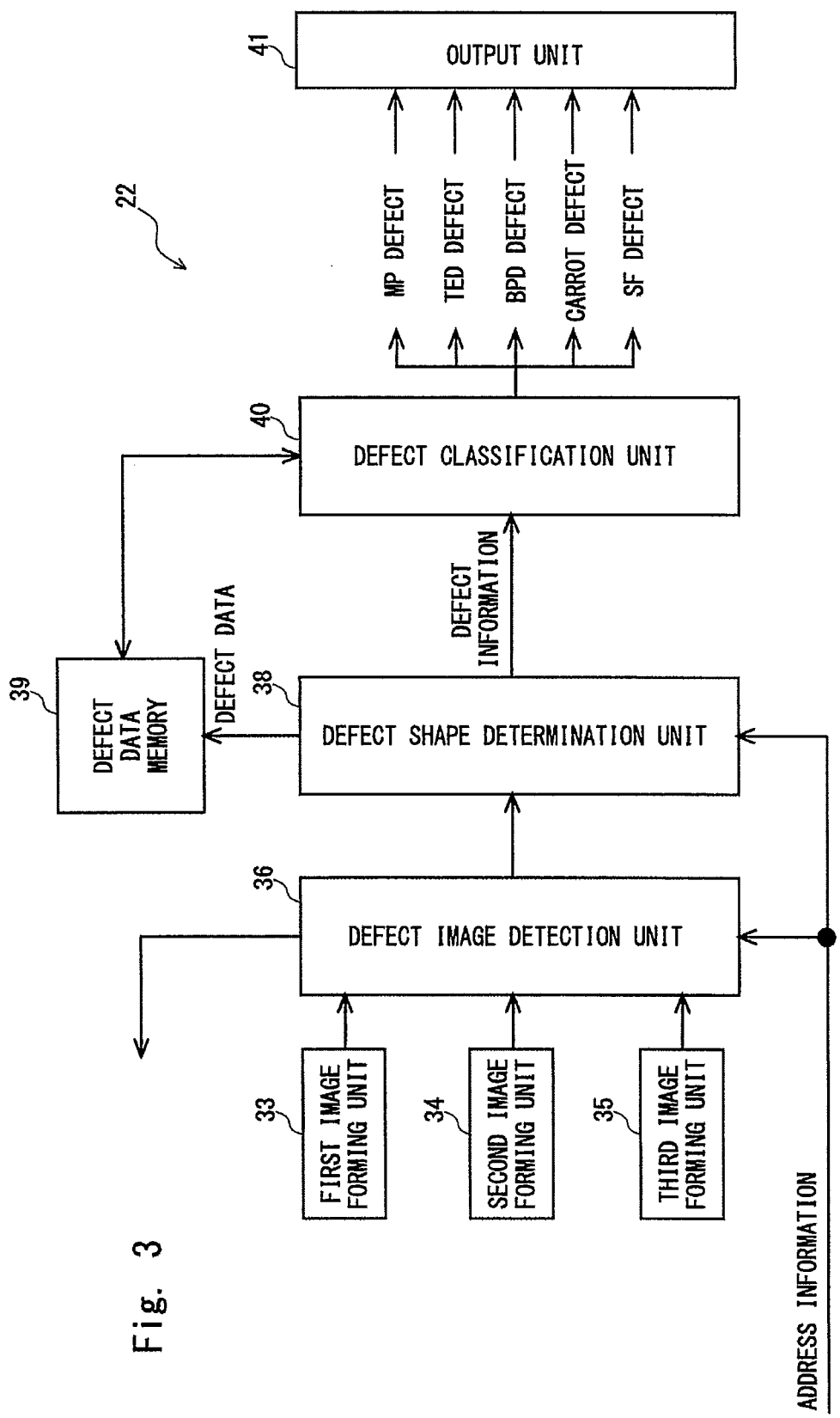
FIG. 3 is a diagram showing a modified example of the signal processor.

FIG. 3 is a diagram showing a modified example of the signal processor 22. The components of the modified example identical to those shown in FIG. 2 are denoted by the same reference numerals, and the description thereof is omitted. In this example, the defect shape determination unit 38 creates defect data information including shape information, size information, and address information on each defect image, and writes the created defect data information into the defect data memory 39. In other words, the defect shape determination unit 38 stores the detected defect images in the defect data memory 39 without distinguishing the defect image detected in the reflection image inspection from the defect image detected in the photoluminescence image inspection. The defect data memory 39 stores the defect data on the defect image of the reflection image and the defect data on the defect image of the photoluminescence image on the basis of an address indicating the position of each defect.

The defect shape determination unit 38 supplies the defect classification unit 40 with defect information including the identification number and the address of each defect as the defect information to be classified. Upon receiving the defect information, the defect classification unit 40 accesses the defect data memory 39. Then the defect classification unit 40 acquires defect data at the address included in the received defect information, and classifies the defect based on the acquired defect data. The defect existing at the address is classified based on the shape and characteristics of the defect image of the reflection image and the shape and characteristics of the defect image of the photoluminescence image at the address designated in the defect information. For example, when a line-shaped defect image exists in the photoluminescence image and when no defect image exists in the reflection image, the defect classification unit 40 determines that a basal plane dislocation exists at the address. When a line-shaped defect image of the photoluminescence image exists at the address included in the defect information and when the line-shaped defect image also exists in the reflection image, the defect classification unit 40 determines that a carrot defect exists at the address. In this example, the photoluminescence image and the reflection image, which are individually detected, are associated with each other by using the address indicating the position of each defect. Accordingly, the defect classification unit 40 can classify each defect at an address site by designating the address of the defect.

Figure 4:
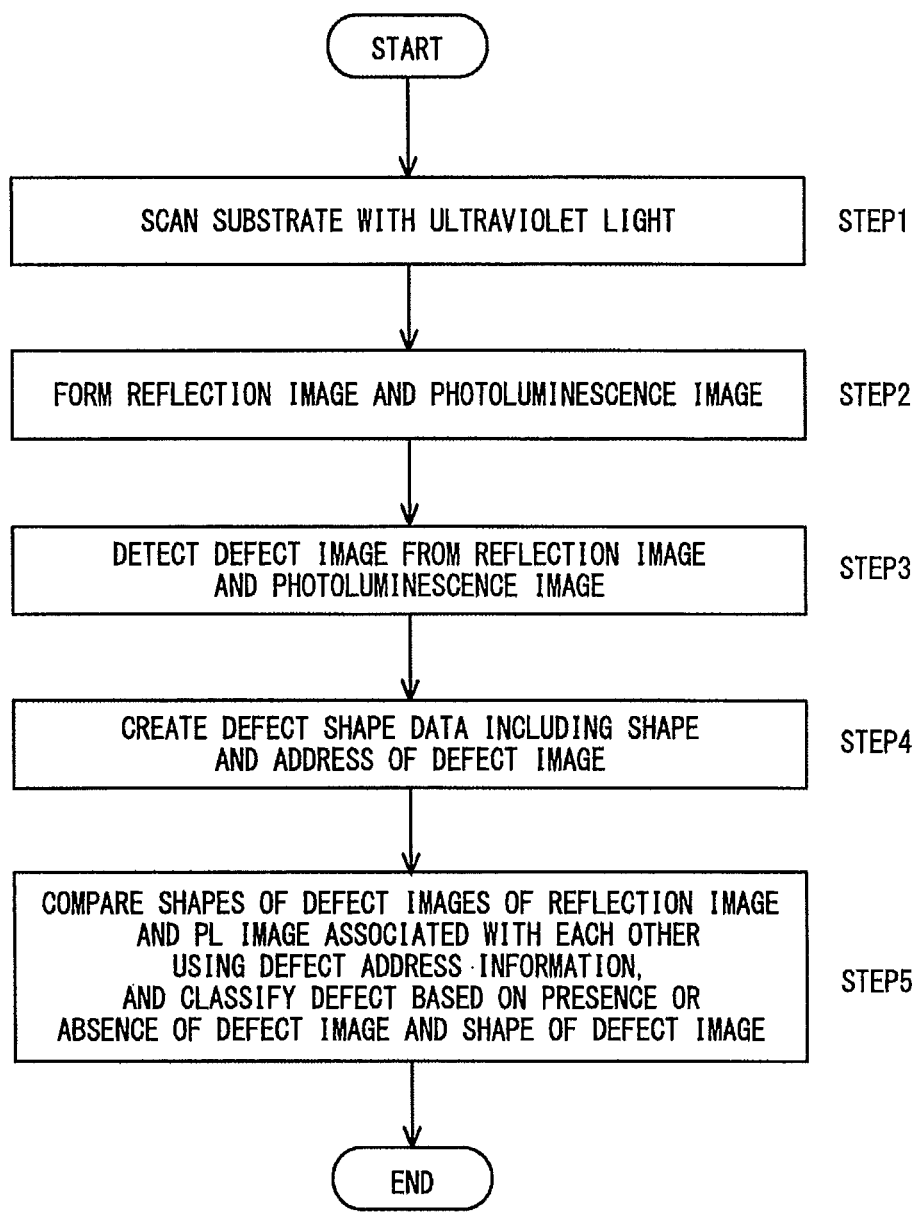
FIG. 4 is a flowchart showing an algorithm for a defect classifying method according to the present invention.

FIG. 4 is a flowchart showing an algorithm for classification of defects according to the present invention. The entire surface of the silicon carbide substrate 16 is scanned with the illumination beam of ultraviolet light (step 1). Reflected light and photoluminescence light, which are emitted from the silicon carbide substrate 16, are individually detected, and a reflection image and a photoluminescence image are formed (step 2).

The reflected light inspection is performed on the formed reflection image to thereby detect a defect image. At the same time, the photoluminescence light inspection is performed on the photoluminescence image, to thereby detect a defect image (step 3).

The shape of each of the detected defect images is specified, and defect data including the shape, characteristics, and address of each defect image is created (step 4). In this case, the defect data includes address information on each defect. Accordingly, the defect image of the reflection image and the defect image of the photoluminescence image are associated with each other by the address of each detect.

Subsequently, each defect is classified based on the defect data. When a defect of the reflection image is input, the defect shape data on the photoluminescence image is referred to by using the address information on the defect. Further, when a defect of the photoluminescence image is input, the defect shape data on the reflection image is referred to by using the address information included in the defect shape data. The defect is classified based on the shape of the defect image and the presence or absence of the defect image (step 5). All defects specific to the epitaxial layer can be classified by the above-mentioned steps 1 to 5.

First Modified Example

Figure 5:
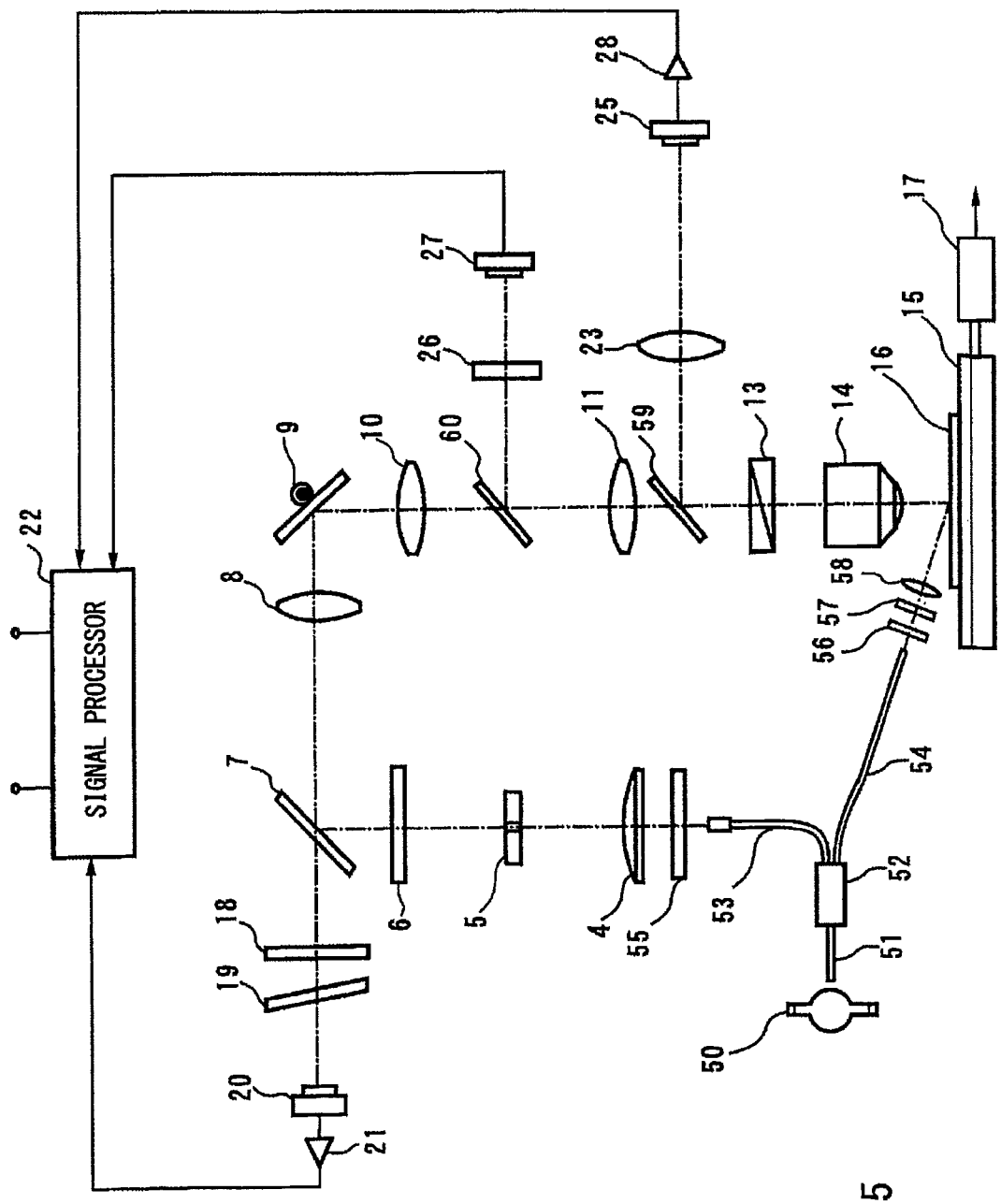
FIG. 5 is a diagram showing a modified example of the inspection apparatus according to the present invention.

FIG. 5 is a diagram showing a first modified example of the inspection apparatus according to the present invention. The components of the first modified example identical to those shown in FIG. 1 are denoted by the same reference numerals, and the description thereof is omitted. In this example, a first illumination system that forms a reflection image and a second illumination system that forms a photoluminescence image are used. In the first illumination system, the surface of the substrate is scanned with the illumination beam of the visible region. In the second illumination system, the surface of the substrate is scanned with the illumination beam of the ultraviolet region. The first and second illumination beams are illuminated at the same location on the silicon carbide substrate 16.

The reflected light inspection is performed by using a mercury lamp 50 as the illumination light source and by using the visible light having a wavelength of 546 nm and emitted from the mercury lamp 50 as the illumination beam of the first illumination system. Further, the photoluminescence light inspection is performed by using the ultraviolet light having a wavelength of 313 nm as the illumination beam of the second illumination system. The light beam emitted from the mercury lamp 50 propagates through a first optical fiber 51. An optical fiber coupler 52 is connected to an output end of the first optical fiber. Second and third optical fibers 53 and 54 are each connected to the output side of the optical fiber coupler 52. The light beam is divided into two light beams by the optical fiber coupler 52. One of the light beams propagates through the second optical fiber 53 and is used for the reflected light inspection, and the other light beam propagates through the third optical fiber 54 and is used for the photoluminescence light inspection.

The light beam emitted from the second optical fiber 53 is directed onto a filter 55. The filter 55 is, for example, a band-pass filter that transmits light having a wavelength of 546 nm. Accordingly, the first illumination beam having a wavelength of 546 nm is emitted from the filter 55. The light beam emitted from the third optical fiber 54 is directed onto a filter 56. The filter 56 is, for example, a band-pass filter that transmits light having a wavelength of 313 nm. The second illumination beam having a wavelength of 313 nm is emitted from the filter 56. The second illumination beam which has passed through the filter 56 is directed onto a polarizer 57. The polarizer 57 emits a p-polarized light beam obtained from the incident light beam.

Accordingly, the second illumination beam which is p-polarized light and has a wavelength of 313 nm is emitted from the polarizer 57. The second illumination beam from the polarizer 57 is converted into a convergent illumination beam by a converging lens 58. The converging lens 58 projects the second illumination beam toward the silicon carbide substrate 16.

The second illumination system projects the p-polarized second illumination beam toward the silicon carbide substrate 16 at an incident angle equal to Brewster's angle. Accordingly, the optical axis of each of the third optical fiber 54, the filter 56, the polarizer 57, and the lens 58, which constitute the second illumination system, is located at an angle equal to Brewster's angle. If the p-polarized second illumination beam is projected at the incident angle equal to Brewster's angle, the reflected light becomes substantially zero, and most of the illumination beam incident on the silicon carbide substrate 16 enters the substrate. Accordingly, photoluminescence light having a higher intensity can be generated and thus a clear photoluminescence image can be formed. This results in achieving an advantage that the accuracy of detecting defect images can be increased and the defect classification can be performed with high accuracy.

In this example, a first dichroic mirror 59 is used instead of the first dichroic mirror 12. The first dichroic mirror 59 reflects light having a wavelength of 700 nm or more and transmits light having a wavelength of 700 nm or less. Accordingly, the reflected light reflected on the silicon carbide substrate 16 is condensed by the objective lens 14, is transmitted through the first dichroic mirror 59, and is directed onto the first photodetector 20. The photoluminescence light emitted from the silicon carbide substrate is condensed by the objective lens 14, is reflected by the first dichroic mirror 59, and is directed onto the second photodetector 25.

Further, in this example, a second dichroic mirror 60 is disposed on the optical path between the first relay lens 10 and the second relay lens 11. For example, the second dichroic mirror 60 reflects light having a wavelength of 390 nm or less, and transmits light having a wavelength of more than 390 nm. The band-pass filter 26, which transmits light having a wavelength in the range of 380 nm±5 nm, and the third photodetector 27 are disposed on the reflected light path of the second dichroic mirror 60. The photoluminescence light resulting from band-edge emission is directed onto the third photodetector 27. Accordingly, the third photodetector 27 can detect the photoluminescence light resulting from band-edge emission. The output signal output from the third photodetector is supplied to the signal processor 22. The signal processor 22 detects a defect based on the output signals output from the first to third photodetectors, and classifies the detected defect.

In this example, a mercury lamp is used as the illumination light source and an illumination beam having a wavelength of 546 nm and an illumination beam having a wavelength of 313 nm are used. Alternatively, a light source that produces visible light or infrared light and another light source that produces ultraviolet light can be used.

Second Modified Example

Figure 6:
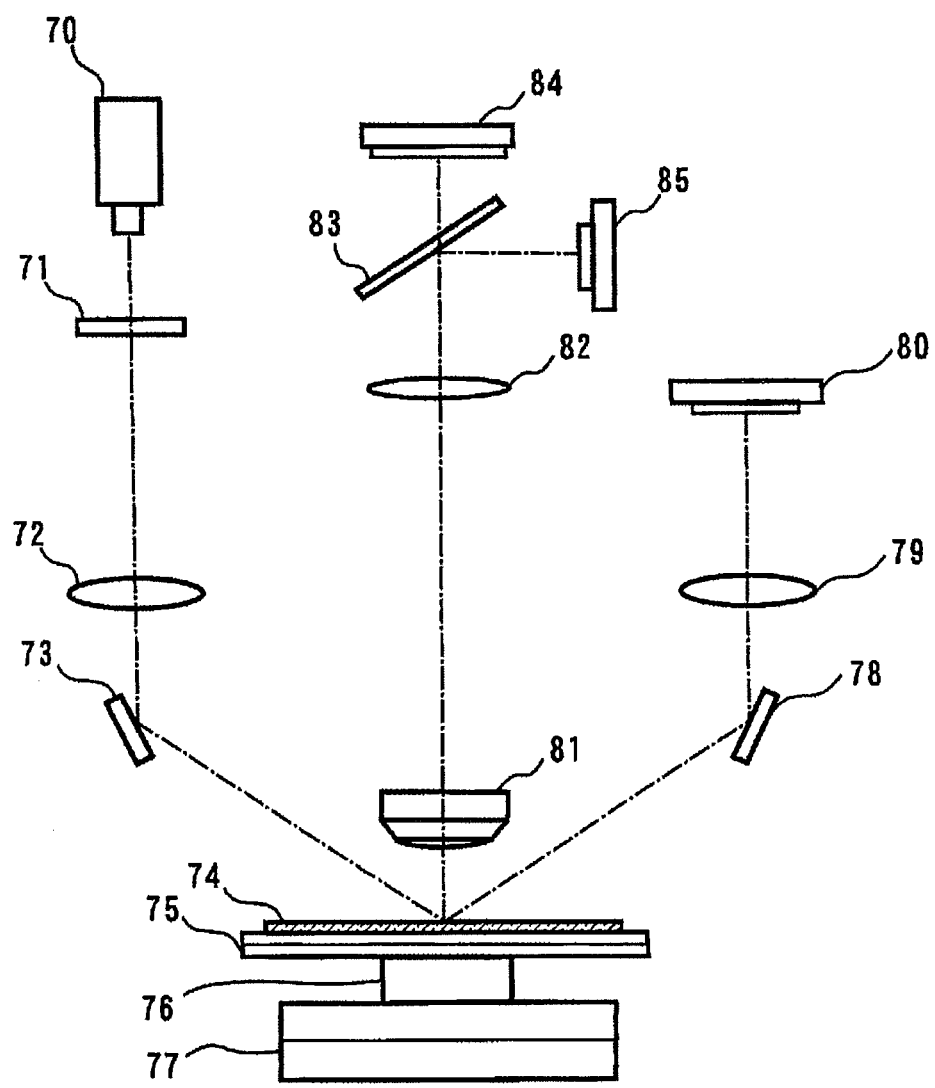
FIG. 6 is a diagram showing a modified example of the inspection apparatus according to the present invention.

FIG. 6 shows a second modified example of the inspection apparatus according to the present invention. In this example, an illumination beam is obliquely projected on the surface of the silicon carbide substrate 16. A reflection image, a scattered light image, and a photoluminescence image are individually captured. The inspection apparatus detects defect images from these images. The inspection apparatus classifies each defect based on the defect image of the photoluminescence image and the defect image of the reflection image. Further, the inspection apparatus classifies each defect based on the defect image of the photoluminescence image and the defect image of the scattered light image. These images are associated with each other by using address information on each of the detected defect images.

A laser light source 70 that emits illumination light of the ultraviolet region is used as the illumination light source. The illumination beam emitted from the laser light source 70 is obliquely projected toward a silicon carbide substrate 74 through a polarizer 71, a converging lens 72, and a total reflection mirror 73. The silicon carbide substrate 74 is held on a stage 75. A motor 76 is connected to the stage 75. The motor 76 is placed on an XY stage 77. The rotation axis of the motor 76 is perpendicular to the X-direction and the Y-direction. A linear movement of the XY stage 77 allows the silicon carbide substrate 74 to linearly move and rotate in accordance with the rotation of the motor 76. Accordingly, the rotation of the motor and the linear movement of the XY stage allow the entire surface of the silicon carbide substrate to be scanned along a spiral trajectory.

When the illumination beam is directed onto the silicon carbide substrate 74, the regularly reflected light reflected on the surface of the substrate and the scattered light generated on the surface of the substrate are emitted. A part of the illumination beam enters the silicon carbide substrate 74. When the illumination beam is directed onto a defect existing in the silicon carbide substrate 74, the photoluminescence light is emitted. The reflected light reflected on the surface of the silicon carbide substrate 74 is reflected by a total reflection mirror 78. The reflected light reflected by the total reflection mirror 78 is directed onto a first photodetector 80 through an imaging lens 79. An output signal from the first photodetector 80 is supplied to the signal processor, and a reflection image of the silicon carbide substrate 74 is formed.

The scattered light generated on a surface the silicon carbide substrate 74 and the photoluminescence light generated in the substrate are condensed by an objective lens 81. The scattered light and the photoluminescence light, which are condensed by the objective lens 81, are directed onto a dichroic mirror 83 through a lens 82. The dichroic mirror 83 is configured to reflect light having a wavelength of 700 nm or more and transmit light having a wavelength of 700 nm or less. Accordingly, the scattered light generated on the surface of the silicon carbide substrate 74 is transmitted through the dichroic mirror 83 and is directed onto a second photodetector 84. The photoluminescence light emitted from the silicon carbide substrate 74 is reflected by the dichroic mirror 83 and is directed onto a third photodetector 85. The second photodetector 84 is composed of a photomultiplier having a sensitivity in the ultraviolet region. The third photodetector 85 is composed of a photomultiplier having a sensitivity in the infrared region. Output signals output from the second photodetector 84 and the third photodetector 85 are supplied to the signal processor, and a scattered light image and a photoluminescence image are formed.

In this example, defects can be classified using both the photoluminescence image and the reflection image. Alternatively, defects can be classified using both the photoluminescence image and the scattered light image. That is, it is possible to classify the detected defects by performing the signal processing shown in FIG. 2 or 3 by using the output signal output from the third photodetector 85 and the output signal output from the first or second photodetector. It is also possible to classify the detected defects by using three types of images, i.e., the photoluminescence image, the scattered light image, and the reflection image.

Third Modified Example

Figure 7:
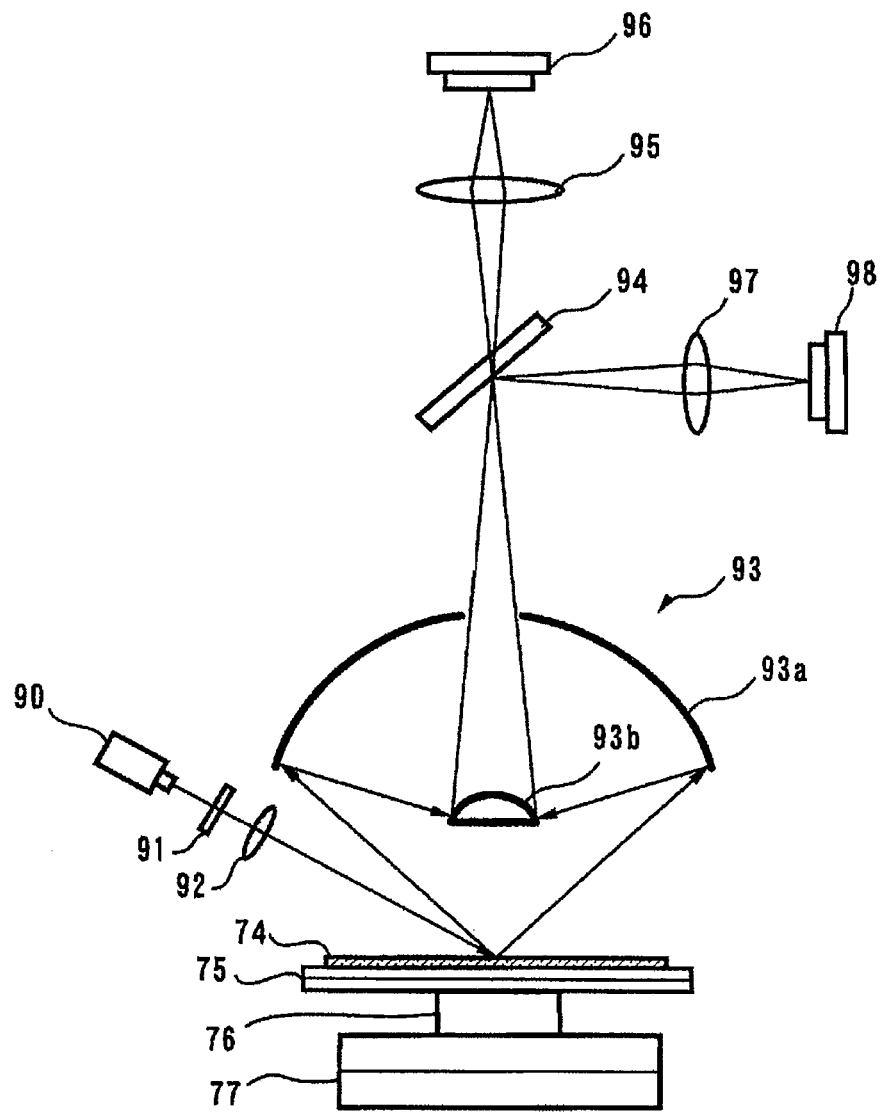
FIG. 7 is a diagram showing a modified example of the inspection apparatus according to the present invention.

FIG. 7 shows a third modified example of the inspection apparatus according to the present invention. In this example, an objective mirror is used instead of the objective lens. Scattered light and photoluminescence light, which are emitted from the silicon carbide substrate 74, are detected through the objective mirror. Defects are detected using a scattered light image and a photoluminescence image, and the detected defects are classified. The components of the third modified example identical to those shown in FIG. 6 are denoted by the same reference numerals, and the description thereof is omitted. A laser light source 90 that emits illumination light of the ultraviolet region is used as the illumination light source. The illumination beam emitted from the laser light source 90 passes through a polarizer 91 and is converted into a convergent beam by a lens 92. The illumination beam emitted from the lens 92 is obliquely projected toward the silicon carbide substrate 74. The silicon carbide substrate 74 is held on the stage 75. The motor 76 is connected to the stage 75. The motor 76 is placed on the XY stage 77. The linear movement of the XY stage 77 and the rotation of the motor 76 allow the entire surface of the silicon carbide substrate 74 to be scanned along a spiral trajectory.

When a defect exists on the surface of the silicon carbide substrate 74, scattered light is generated due to the defect. A part of the illumination beam enters the silicon carbide substrate 74 and is directed onto a defect existing in the silicon carbide substrate 74. Then photoluminescence light is emitted from the silicon carbide substrate 74. The scattered light and the photoluminescence light, which are emitted from the silicon carbide substrate 7, are condensed by an objective 93. The objective 93 includes a concave mirror 93a and a convex mirror 93b. The scattered light and photoluminescence light, which are emitted from the silicon carbide substrate 74, are reflected by the concave mirror 93a and the convex mirror 93b, respectively. Further, the scattered light and the photoluminescence light are directed onto a dichroic mirror 94 through an opening which is formed in the concave mirror 93a. The dichroic mirror 94 reflects light having a wavelength of 700 nm or more and transmits light having a wavelength of 700 nm or less. The scattered light emitted from the silicon carbide substrate 74 is transmitted through the dichroic mirror 94 and is directed onto a first photodetector 96 through a lens 95. An output signal from the first photodetector 96 is supplied to the signal processor, and a scattered light image of the silicon carbide substrate 74 is formed.

The photoluminescence light emitted from the silicon carbide substrate 74 is reflected by the dichroic mirror 94. The photoluminescence light reflected by the dichroic mirror 94 is directed onto a second photodetector 98 through a lens 97. An output signal from the second photodetector 98 is supplied to the signal processor, so that a photoluminescence image is formed. The signal processor performs signal processing as described above to detect a defect which is present at the silicon carbide substrate, and classifies the detected defect. As with the reflection image, the scattered light image forms a defect image of a defect appearing on the surface of the substrate. The photoluminescence image forms a defect image of a defect existing in the substrate. Accordingly, it is possible to detect both a defect appearing on the surface of the substrate and a defect existing in the substrate. In this manner, the scattered light is used instead of the reflected light in the third modified example.

In this exemplary embodiment, the inspection apparatus may conduct at least two inspections, preferably three inspections, selected from the group consisting of surface inspection using reflected light, surface inspection using scattered light, PL inspection using a band-edge emission wavelength, PL inspection using visible light, and PL inspection using near-infrared light. Further, the inspection apparatus can distinguish the defects based on the results of two or more inspections. For example, the inspection apparatus can distinguish the defects in accordance with a table illustrated in FIG. 8. The defects can be adequately classified using the table illustrated in FIG. 8.

The present invention is not limited only to the above exemplary embodiments and can be modified and changed in various manners. In the above exemplary embodiments, the differential interference image is used as the reflection image. However, a normal reflection image can also be used instead of the differential interference image. Specifically, the illumination beam emitted from the illumination light source is projected toward the silicon carbide substrate through an objective lens, and the reflection image formed when the reflected light, which is reflected on the surface of the silicon carbide substrate, is received by a two-dimensional imaging device or a line sensor through the objective lens can be used.

The signal processor 22 is a personal computer or the like and executes the process as described above. The units of the signal processor 22 may each be configured, as hardware, by a CPU, memory, or a circuit in another form, or, as software, by a program loaded into a memory. Accordingly, these function blocks may be realized in a form of hardware, software, or a combination of the two as commonly understood by persons having ordinary skill in the art, and are not be limited to any specific form. Further, it is to be noted that the elements having substantially the same features depicted in the drawings will be assigned the same reference numerals, and the description thereof will not be repeated as appropriate.

Further, the program may be stored by using various types of non-transitory computer readable medium, and supplied to computers. The non-transitory computer readable medium includes various types of tangible storage medium. Examples of the non-transitory computer readable medium include a magnetic recording medium (such as a flexible disk, a magnetic tape, and a hard disk drive), a magneto-optic recording medium (such as a magneto-optic disk), a CD-ROM (Read Only Memory), a CD-R, and a CD-R/W, and a semiconductor memory (such as a mask ROM, a PROM (Programmable ROM), an EPROM (Erasable PROM), a flash ROM, and a RAM (Random Access Memory)). Further, the program may be supplied to computers by using various types of transitory computer readable media. Examples of the transitory computer readable media include an electrical signal, an optical signal, and an electromagnetic wave. The transitory computer readable media may be used to supply programs to computer through a wire communication path such as an electrical wire and an optical fiber, or wireless communication path.

From the invention thus described, it will be obvious that the embodiments of the invention may be varied in many ways. Such variations are not to be regarded as a departure from the spirit and scope of the invention, and all such modifications as would be obvious to one skilled in the art are intended for inclusion within the scope of the following claims.

What is claimed is:

1. A defect classifying method that detects a defect which is present at a silicon carbide substrate and classifies the defect by distinguishing a basal plane dislocation from other crystal defects, the defect classifying method comprising:
    projecting an illumination beam toward the silicon carbide substrate and scanning the silicon carbide substrate with the illumination beam;
    condensing reflected light and photoluminescence light emitted from the silicon carbide substrate;
    separating, from the condensed light, each of reflected light and photoluminescence light of a visible region or an infrared region, and detecting each of the reflected light and the photoluminescence light of the visible region or the infrared region;
    a first inspection step of detecting a defect from the detected reflected light and detecting a defect image of the reflected light;
    a second inspection step of detecting a defect from the detected photoluminescence light and detecting a defect image of the photoluminescence light; and
    a defect classification step of classifying each defect detected in the first and second inspection steps,
    wherein when the defect image of the photoluminescence light is detected in the second inspection step, the defect is classified with reference to a result of a reflected light inspection in the first inspection step.

2. The defect classifying method according to claim 1, wherein when the defect image of the photoluminescence light is detected in the second inspection step and when the defect image of the reflected light is not detected at the same address as a defect address detected in the second inspection step in the first inspection step, or a defect image having a contrast luminance distribution is detected in the first inspection step, the detected defect is classified as a basal plane dislocation.

3. The defect classifying method according to claim 2, wherein when a line-shaped defect image of the photoluminescence light is detected in the second inspection step and when the defect image of the reflected light is not detected at the same address as the defect address detected in the second inspection step in the first inspection step, or the defect image of the reflected light having a contrast luminance distribution is detected in the first inspection step, the detected defect is classified as the basal plane dislocation.

4. The defect classifying method according to claim 1, wherein when a line-shaped defect image of the photoluminescence light is detected in the second inspection step and a line-shaped defect image of the reflected light is detected at the same address as a defect address detected in the second inspection step in the first inspection step, the detected defect is classified as a carrot defect.

5. The defect classifying method according to claim 1, wherein the defect image of the reflected light formed in the first inspection step is a differential interference image.

6. A defect classifying method that detects a defect which is present at a silicon carbide substrate and classifies the defect by distinguishing a basal plane dislocation from other defects, the defect classifying method comprising:
    projecting an illumination beam toward the silicon carbide substrate and scanning the silicon carbide substrate with the illumination beam;
    condensing scattered light and photoluminescence light emitted from the silicon carbide substrate;
    separating, from the condensed light, each of scattered light and photoluminescence light of a visible region or an infrared region, and detecting each of the scattered light and the photoluminescence light of the visible region or the infrared region;
    a first inspection step of detecting a defect from the detected scattered light and forming a defect image of the scattered light;
    a second inspection step of detecting a defect from the detected photoluminescence light and forming a defect image of the photoluminescence light; and
    a defect classification step of classifying each defect detected in the first and second inspection steps,
    wherein when the defect image of the photoluminescence light is detected in the second inspection step, the defect is classified with reference to a result of a scattered light inspection in the first inspection step.

7. The defect classifying method according to claim 6, wherein when the defect image of the photoluminescence light is detected in the second inspection step and no defect image is detected at the same address as a defect address detected in the second inspection step in the fast inspection step, the detected defect is classified as the basal plane dislocation.

8. The defect classifying method according to claim 6, wherein the illumination beam is formed of ultraviolet light and is obliquely projected on a surface of the silicon carbide substrate.

9. A defect classifying method that classifies a defect by distinguishing a basal plane dislocation which is present at a silicon carbide substrate from other crystal defects, the defect classifying method comprising:
    projecting an illumination beam toward the silicon carbide substrate and scanning the silicon carbide substrate with the illumination beam;
    condensing reflected light and photoluminescence light emitted from the silicon carbide substrate;
    separating, from the condensed light, reflected light, photoluminescence light of a first wavelength region corresponding to a band-edge emission wavelength, and photoluminescence light of a second wavelength region having a wavelength longer than that of the first wavelength region, and detecting each of the reflected light, the photoluminescence light of a first wavelength region and the photoluminescence light of a second wavelength region;
    a first inspection step of detecting a defect from the detected reflected light and forming a defect image of the reflected light;
    a second inspection step of detecting a defect from the detected photoluminescence light of the first wavelength region and forming a defect image of the photoluminescence light of the first wavelength region;
a third inspection step of detecting a defect from the detected photoluminescence light of the second wavelength region and forming a defect image of the photoluminescence light of the second wavelength region; and
a defect classification step of classifying each defect detected in the first to third inspection steps,
wherein when the defect image of the photoluminescence light of the second wavelength region is detected in the third inspection step, the detected defect is classified with reference to a result of a reflected light inspection in the first inspection step.

10. The defect classifying method according to claim 9, wherein when the defect image of the photoluminescence light of the second wavelength region is detected in the third inspection step and when no defect image is detected in the first inspection step, or a defect image having a contrast luminance distribution is detected in the first inspection step, the defect is classified as the basal plane dislocation.

11. The defect classifying method according to claim 9, wherein the first wavelength region is set to a wavelength equal to a band-edge emission wavelength of silicon carbide, or a wavelength in the vicinity of the band-edge emission wavelength, and the second wavelength region is set to a visible region or an infrared region.

12. The defect classifying method according to claim 9, wherein the first wavelength region is set to a near infrared region, and the second wavelength region is set to a visible region,
when the low luminance defect is detected in the second inspection step, and when a high luminance is detected in the third inspection step, the defect is classified as a stacking fault.

13. An inspection apparatus that detects a defect which is present at a silicon carbide substrate and classifies the defect by distinguishing a basal plane dislocation from other crystal defects, the inspection apparatus comprising:
an illumination unit that includes a light source that produces an illumination beam, and projects the illumination beam emitted from the light source toward the silicon carbide substrate;
a scanner that scans a surface of the silicon carbide substrate with the illumination beam;
an objective lens that condenses reflected light and photoluminescence light emitted from the silicon carbide substrate;
a separation unit that separates each of reflected light and photoluminescence light of a visible region or an infrared region from the light condensed by the objective lens;
first and second photodetectors that respectively detect the separated reflected light and the separated photoluminescence light of the visible region or the infrared region; and
a signal processor that detects a defect based on output signals output from the first and second photodetectors and classifies the detected defect, wherein
the signal processor includes:
a first defect image detection unit that detects a defect from the output signal output from the first photodetector and detects a defect image of the reflected light;
a second defect image detection unit that detects a defect from the output signal output from the second photodetector and detects a defect image of the photoluminescence light; and
a defect classification unit that classifies each defect detected by the first and second defect image detection units, and
when the defect image of the photoluminescence light is detected by the second defect image detection unit, the defect classification unit classifies the detected defect with reference to a result of a reflected light inspection performed by the first defect image detection unit.

14. The inspection apparatus according to claim 13, wherein when the defect image of the photoluminescence light is detected by the second defect image detection unit and when the defect image of the reflected light is not detected at the same address as a defect address detected in the second defect image detection unit in the reflected light inspection performed by the first defect image detection unit, or a defect image of the reflected light having a contrast luminance distribution is detected in the reflected light inspection, the defect classification unit classifies the detected defect as a basal plane dislocation.

15. The inspection apparatus according to claim 13, wherein
the signal processor further includes:
a unit that creates defect data including information indicating a shape and a position of the defect image detected by the first and second defect image detection units; and
a storage unit that stores the created defect data,
the defect classification unit receives, as defect information to be classified, information including a shape and an address of a defect, and
upon receiving the defect information to be classified, the defect classification unit accesses the storage unit and classifies the defect with reference to the presence or absence of a defect image at the address included in the received defect information and the shape of the defect image.

16. The inspection apparatus according to claim 15, wherein
the storage unit includes:
a first defect data memory that stores defect data including information indicating a shape and a position of the defect image of the reflected light detected by the first defect image detection unit; and
a second defect data memory that stores defect data including information indicating a shape and a position of the defect image of the photoluminescence light detected by the second defect image detection unit.

17. The inspection apparatus according to claim 16, wherein
the defect classification unit includes:
a first classification that classifies the defect detected by the second defect image detection unit;
a second classification unit that classifies the defect detected by the first defect image detection unit,
upon receiving the defect information to be classified, the first classification unit accesses the first defect data memory and classifies the defect with reference to the presence or absence of a defect image at a corresponding address and the shape of the defect image, and
upon receiving the defect information to be classified, the second classification unit accesses the second defect data memory and classifies the defect with reference to the presence or absence of a defect image at a corresponding address and the shape of the defect image.

18. The inspection apparatus according to claim 13, wherein the illumination unit includes:
a first illumination system that projects a first illumination beam of a visible region toward the silicon carbide substrate at a substantially vertical incident angle; and
a second illumination system that projects a second illumination beam of a ultraviolet region toward the silicon carbide substrate at an oblique incident angle, and the first and second illumination beams are illuminated at a location of the silicon carbide substrate.

19. The inspection apparatus according to claim 18, wherein the second illumination system projects a p-polarized illumination beam of the ultraviolet region toward the silicon carbide substrate at an incident angle substantially equal to Brewster's angle.

20. The inspection apparatus according to claim 13, further comprising:
a unit that selectively disperses photoluminescence light of a band-edge emission wavelength region from light condensed by the objective lens; and
a third photodetector that receives band-edge emission light,
wherein the signal processor detects a defect by using output signals output from the first to third photodetectors.

21. An inspection apparatus that detects a defect which is present at a silicon carbide substrate and classifies the defect by distinguishing a basal plane dislocation from other crystal defects, the inspection apparatus comprising:
an illumination unit that includes a light source that produces an illumination beam of an ultraviolet region, and obliquely projects the illumination beam emitted from the light source toward the silicon carbide substrate;
a scanner that scans the silicon carbide substrate with the illumination beam;
a unit that condenses scattered light and photoluminescence light emitted from the silicon carbide substrate;
a separation unit that separates, from the condensed light, each of scattered light and photoluminescence light of a visible region or an infrared region;
first and second photodetectors that respectively detect the separated scattered light and the separated photoluminescence light of the visible region or the infrared region; and
a signal processor that detects a defect based on output signals output from the first and second photodetectors and classifying the detected defect, wherein the signal processor includes:
a first defect image detection unit that detects a defect from the output signal output from the first photodetector and forms a defect image of the scattered light;
a second defect image detection unit that detects a defect from the output signal output from the second photodetector and forms a defect image of the photoluminescence light; and
a defect classification unit that classifies each defect detected by the first and second defect image detection units, and when the defect image of the photoluminescence light is detected by the second defect image detection unit, the defect classification unit classifies the detected defect with reference to a result of a scattered light inspection performed by the first defect image detection unit.

22. The inspection apparatus according to claim 21, wherein when the defect image of the photoluminescence light is detected by the second defect image detection unit and the defect image of the scattered light is not detected at the same address as a defect address detected by the second defect image detection unit in the scattered light inspection performed by the first defect image detection unit, the defect classification unit classifies the detected defect as a basal plane dislocation.

23. A defect classifying method that detects a defect which is present at a silicon carbide substrate or a silicon carbide substrate having an epitaxial layer formed thereon, and classifies the defect by distinguishing a basal plane dislocation from other defects, the defect classifying method comprising:
projecting illumination light of an ultraviolet region toward the silicon carbide substrate and scanning the silicon carbide substrate with the illumination light of the ultraviolet region;
condensing reflected light and photoluminescence light emitted from the silicon carbide substrate;
separating each of the reflected light and the photoluminescence light from the condensed light, and detecting each of the separated reflected light and the separated photoluminescence light;
a first defect detection step of detecting a defect from the detected reflected light to perform defect detection using the reflected light;
a second defect detection step of detecting a defect from the detected photoluminescence light to perform defect detection using the photoluminescence light;
a defect classification step of classifying each defect detected in the first and second defect detection steps; and
simultaneously performing the defect detection using the reflected light and the defect detection using the photoluminescence light,
wherein in the defect classification step, the basal plane dislocation is distinguished by using both a result of the defect detection using the reflected light and a result of the defect detection using the photoluminescence light.

24. The defect classifying method according to claim 23, wherein the illumination light is illumination light having energy larger than band-gap energy of silicon carbide.

25. The defect classifying method according to claim 23, wherein when a defect is detected from the photoluminescence light in the second defect detection step and no defect is detected from the reflected light in the first defect detection step, the detected defect is classified as the basal plane dislocation.

26. A defect classifying method that detects a defect which is present at a silicon carbide substrate or a silicon carbide substrate having an epitaxial layer formed thereon, and classifies the defect by distinguishing a basal plane dislocation from other crystal defects, the defect classifying method comprising:
projecting illumination light of an ultraviolet region toward the silicon carbide substrate and scanning the silicon carbide substrate with the illumination light;
condensing scattered light and photoluminescence light emitted from the silicon carbide substrate;
separating each of the scattered light and the photoluminescence light from the condensed light, and detecting each of the scattered light and the photoluminescence light;

a first defect detection step of detecting a defect from the detected scattered light;

a second defect detection step of detecting a defect from the detected photoluminescence light; and a defect classification step of classifying each defect detected in the first and second defect detection steps, wherein simultaneously performing the defect detection using the scattered light and the defect detection using the photoluminescence light, and in the defect classification step, the basal plane dislocation is distinguished by using both a result of the defect detection using the scattered light and a result of the defect detection using the photoluminescence light.

27. The defect classifying method according to claim 26, wherein when a defect is detected in the second defect detection step and no defect is detected in the first defect detection step, the detected defect is classified as the basal plane dislocation.

28. The defect classifying method according to claim 26, wherein the illumination light is obliquely projected on the silicon carbide substrate.

29. A defect classifying method that detects a crystal defect which is present at a silicon carbide substrate or a silicon carbide substrate having an epitaxial layer formed thereon, and classifies the detected crystal defect, the defect classifying method comprising:

projecting illumination light of an ultraviolet region toward the silicon carbide substrate and scanning the silicon carbide substrate with the illumination light;

condensing reflected light and photoluminescence light emitted from the silicon carbide substrate;

separating, from the condensed light, each of reflected light, photoluminescence light having a first wavelength region including a band-edge emission wavelength of silicon carbide, and photoluminescence light having a second wavelength region including a wavelength longer than that of the first wavelength region, and detecting each of the reflected light and the first and second photoluminescence lights;

a first defect detection step of detecting a defect from the detected reflected light;

a second defect detection step of detecting a defect from the detected photoluminescence light having the first wavelength region;

a third defect detection step of detecting a defect from the detected photoluminescence light having the second wavelength region; and a defect classification step of classifying each defect detected in the first to third defect detection steps, wherein in the defect classification step, the basal plane dislocation is distinguished by using both a result of defect detection using the reflected light and a result of defect detection using the photoluminescence light having the second wavelength region.

30. The defect classifying method according to claim 29, wherein the first wavelength region is set to a near infrared region, and the second wavelength region is set to a visible region, when the low luminance defect is detected in the second inspection step, and when a high luminance is detected in the third inspection step, the defect is classified as a stacking fault.

31. The defect classifying method according to claim 29, wherein when a defect is detected in the third defect detection step and no defect is detected in the first defect detection step, the detected defect is distinguished as the basal plane dislocation, and when a defect is detected in the third defect detection step and a defect is detected in the first defect detection step, the detected defect is distinguished as a carrot defect.

32. The defect classifying method according to claim 29, wherein the first wavelength region is set at a wavelength of 380 nm or in the vicinity of 380 nm, and the second wavelength region is set in a visible region or an infrared region.

33. An inspection apparatus that detects a defect which is present at a silicon carbide substrate or a silicon carbide substrate having an epitaxial layer formed therein, and classifies the defect by distinguishing a basal plane dislocation from other crystal defects, the inspection apparatus comprising:

an illumination unit that projects illumination light of an ultraviolet region toward the silicon carbide substrate to be inspected;

a seamier that scans the silicon carbide substrate with the illumination light;

an objective lens that condenses reflected light and photoluminescence light emitted from the silicon carbide substrate;

a separation unit that separates each of the reflected light and the photoluminescence light from the light focused by the objective lens;

first and second photodetectors that respectively detect the separated reflected light and the separated photoluminescence light; and a signal processor that detects a defect based on output signals output from the first and second photodetectors and classifies the detected defect, wherein the signal processor includes:
a first defect detection unit that detects a defect from the output signal output from the first photodetector;
a second defect detection unit that detects a defect from the output signal output from the second photodetector; and
a defect classification unit that classifies each defect detected by the first and second defect detection units, and the defect classification unit distinguishes the basal plane dislocation by using both a result of defect detection using the reflected light and a result of defect detection using the photoluminescence light.

34. The inspection apparatus according to claim 33, wherein the illumination light is illumination light having energy larger than band-gap energy of silicon carbide.

35. The inspection apparatus according to claim 34, wherein when a defect is detected in the defect detection using the photoluminescence light and no defect is detected in the defect detection using the reflected light, the defect classification unit classifies the detected defect as the basal plane dislocation.

36. The inspection apparatus according to claim 33, further comprising:

a unit that selectively disperses photoluminescence light of a wavelength region including a band-edge emission wavelength of silicon carbide from the light condensed by the objective lens; and a third photodetector that receives the dispersed light of a band-edge emission wavelength region, and the signal processor detects a defect by using output signals output from the first to third photodetectors and classifies the detected defect.

37. An inspection apparatus that detects a defect which is present at a silicon carbide substrate or a silicon carbide substrate having an epitaxial layer formed thereon, and classifies the defect by distinguishing a basal plane dislocation from other crystal defects, the inspection apparatus comprising:
    an illumination unit that obliquely projects illumination light of an ultraviolet region toward a silicon carbide substrate to be inspected;
    a scanner that scans the silicon carbide substrate with the illumination light;
    a unit that condenses scattered light and photoluminescence light emitted from the silicon carbide substrate;
    a separation unit that separates each of the scattered light and the photoluminescence light from the condensed light;
    first and second photodetectors that respectively detect the separated scattered light and the separated photoluminescence light; and
    a signal processor that detects a defect based on output signals output from the first and second photodetectors, and classifies the detected defect, wherein
    the signal processor includes:
        a first defect detection unit that detects a defect from the output signal output from the first photodetector;
        a second defect detection unit that detects a defect from the output signal output from the second photodetector; and
        a defect classification unit that classifies each defect detected by the first and second defect detection units, and
    the defect classification unit distinguishes the basal plane dislocation by using both a result of defect detection using the scattered light and a result of defect detection using the photoluminescence light.

38. The inspection apparatus according to claim 37, wherein the illumination light is illumination light having energy larger than band-gap energy of silicon carbide.

39. The inspection apparatus according to claim 37, wherein when a defect is detected in the defect detection using the photoluminescence light and no defect is detected in the defect detection using the scattered light, the defect classification unit classifies the detected defect as the basal plane dislocation.

40. An inspection apparatus that detects a defect which is present at a silicon carbide substrate or a silicon carbide substrate having an epitaxial layer formed thereon, and classifies the detected defect, the inspection apparatus comprising:
    an illumination unit that illuminates a location on the silicon carbide substrate with first and second illumination beams, the illumination unit including: a first illumination system that vertically projects the first illumination beam having a first wavelength toward the silicon carbide substrate; and a second illumination system that obliquely projects the second illumination beam having a second wavelength different from the first wavelength toward the silicon carbide substrate;
    a scanner that scans the silicon carbide substrate with the first and second illumination beams;
    a condensing unit that condenses reflected light and photoluminescence light emitted from the silicon carbide substrate;
    a separation unit that separates each of the reflected light and the photoluminescence light from the light condensed by the condensing unit;
    a first photodetector that detects the separated reflected light and a second photodetector that detects the separated photoluminescence light; and
    a signal processor that detects a defect based on output signals output from the first and second photodetectors and classifies the detected defect, wherein
    the signal processor includes:
        a first defect detection unit that detects a defect from the output signal output from the first photodetector;
        a second defect detection unit that detects a defect from the output signal output from the second photodetector; and
        a defect classification that classifies each defect detected by the first and second defect detection units,
    simultaneously performing the defect detection using the reflected light and the defect detection using the photoluminescence light, and
    the defect classification unit distinguishes the basal plane dislocation by using both a result of the defect detection using the reflected light and a result of the defect detection using the photoluminescence light.

41. The inspection apparatus according to claim 40, further comprising:
    a unit that selectively disperses photoluminescence light of a wavelength region including a band-edge emission wavelength of silicon carbide from the light condensed by the condensing unit; and
    a third photodetector that receives the dispersed photoluminescence light of a band-edge emission wavelength region,
    the signal processor includes a third defect detection unit that detects a defect from an output signal output from the third photodetector, and
    the defect classification unit classifies each defect detected by the first to third defect detection units.

42. The inspection apparatus according to claim 40, wherein when a defect is detected by the second defect detection unit and no defect is detected by the first defect detection unit, the detected defect is classified as the basal plane dislocation.

43. The inspection apparatus according to claim 40, further comprising:
    a unit that separates a visible photoluminescence light from a near infrared photoluminescence light;
    a third photodetector that receives the near infrared photoluminescence light separated from the visible photoluminescence light; and
    a third defect detection unit that detects a defect from the output signal output from the third photodetector; and
    wherein the second photodetector receives the visible photoluminescence light separated from the near infrared photoluminescence light,
    when a high luminance defect is detected in the second inspection step, and when a low luminance is detected in the third inspection step, the defect is classified as a stacking fault.

44. The inspection apparatus according to claim 40, wherein when a defect is detected by the second defect detection unit and a defect is detected by the first defect detection unit, the detected defect is classified as a carrot defect.

45. The inspection apparatus according to claim 41, wherein the first wavelength is set in a visible region and the second wavelength is set in an ultraviolet region, and a surface of the silicon carbide substrate or a surface of the epitaxial layer is scanned with both visible light and ultraviolet light.

46. The inspection apparatus according to claim 45, wherein the second illumination beam includes p-polarized illumination light of an ultraviolet region, and the surface of the silicon carbide substrate or the surface of the epitaxial layer is illuminated at an incident angle substantially equal to Brewster's angle.

* * * * *